US009429522B2

(12) United States Patent
Swager et al.

(10) Patent No.: US 9,429,522 B2
(45) Date of Patent: Aug. 30, 2016

(54) SENSOR OF SPECIES INCLUDING TOXINS AND CHEMICAL WARFARE AGENTS

(71) Applicant: Massachusetts Institute of Technology, Cambridge, MA (US)

(72) Inventors: Timothy M. Swager, Newton, MA (US); Samuel W. Thomas, III, Quincy, MA (US); Koushik Venkatesan, Zurich (CH)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/332,231

(22) Filed: Jul. 15, 2014

(65) Prior Publication Data

US 2015/0247805 A1    Sep. 3, 2015

Related U.S. Application Data

(63) Continuation of application No. 11/588,881, filed on Oct. 27, 2006, now abandoned.

(51) Int. Cl.
  *G01N 21/64* (2006.01)
  *G01N 21/76* (2006.01)
  (Continued)

(52) U.S. Cl.
  CPC .......... *G01N 21/76* (2013.01); *C07F 15/0086* (2013.01); *C09K 11/06* (2013.01);
  (Continued)

(58) Field of Classification Search
  None
  See application file for complete search history.

(56) References Cited

U.S. PATENT DOCUMENTS

| 3,242,186 A | 3/1966 | Dershowitz |
| 3,785,813 A | 1/1974 | Rickter |

(Continued)

FOREIGN PATENT DOCUMENTS

| DE | 4121138 | 1/1993 |
| DE | 197 44 792 A1 | 4/1999 |

(Continued)

OTHER PUBLICATIONS

[No Author Listed] Chemical Structure for Biphenylene. CAS No. 259-79-0. Downloaded Dec. 12, 2005.

(Continued)

*Primary Examiner* — Yelena G Gakh
*Assistant Examiner* — Michelle Adams
(74) *Attorney, Agent, or Firm* — Wolf, Greenfield & Sacks, P.C.

(57) ABSTRACT

The present invention generally relates to emissive materials, devices, and related methods. In some cases, the present invention provides sensors and methods for the determination of analytes, wherein the analytes may be determined by monitoring, for example, a change in an optical signal of an emissive material upon exposure to an analyte. The analyte and the emissive material may interact via a chemical reaction, such as an oxidative addition reaction, or other chemical, biochemical or biological interaction (e.g., recognition), to form a new emissive species. In some cases, the present invention may be useful in the detection of a wide variety of analytes, such as toxins, chemical warfare agents, and explosives. The present invention also provides emissive compounds, and related methods, including metal complexes that are capable of interacting with an analyte to produce a change in the emission of the compound. Some advantages of the present invention include the determination of analytes with high specificity and sensitivity and the ability to fabricate simplified and highly portable devices.

31 Claims, 14 Drawing Sheets

(51) Int. Cl.
*G01N 33/00* (2006.01)
*C07F 15/00* (2006.01)
*C09K 11/06* (2006.01)
*G01N 33/20* (2006.01)

(52) U.S. Cl.
CPC ......... *G01N 21/64* (2013.01); *G01N 33/0057* (2013.01); *G01N 33/20* (2013.01); *C09K 2211/1007* (2013.01); *C09K 2211/1011* (2013.01); *C09K 2211/1029* (2013.01); *C09K 2211/1092* (2013.01); *C09K 2211/185* (2013.01); *G01N 2201/06113* (2013.01); *Y10T 436/172307* (2015.01); *Y10T 436/196666* (2015.01)

(56) References Cited

U.S. PATENT DOCUMENTS

| | | | |
|---|---|---|---|
| 4,049,616 A | 9/1977 | Scott et al. |
| 4,356,429 A | 10/1982 | Tang |
| 4,513,078 A | 4/1985 | Sandrik et al. |
| 4,539,507 A | 9/1985 | VanSlyke et al. |
| 4,687,732 A | 8/1987 | Ward et al. |
| 4,752,588 A | 6/1988 | Ellis et al. |
| 4,839,112 A | 6/1989 | Wynne et al. |
| 4,841,099 A | 6/1989 | Epstein et al. |
| 4,868,103 A | 9/1989 | Stavrianopoulos et al. |
| 4,883,608 A | 11/1989 | Trujillo et al. |
| 4,894,443 A | 1/1990 | Greenfield et al. |
| 4,927,768 A | 5/1990 | Coughlin et al. |
| 4,946,890 A | 8/1990 | Meador |
| 4,957,615 A | 9/1990 | Ushizawa et al. |
| 4,992,244 A | 2/1991 | Grate |
| 4,992,302 A | 2/1991 | Lindmayer |
| 5,091,502 A | 2/1992 | Narang et al. |
| 5,155,149 A | 10/1992 | Atwater et al. |
| 5,157,261 A | 10/1992 | Grey et al. |
| 5,194,393 A | 3/1993 | Hugl et al. |
| 5,217,715 A | 6/1993 | Krivan et al. |
| 5,236,808 A | 8/1993 | Smothers |
| 5,237,582 A | 8/1993 | Moses |
| 5,244,813 A | 9/1993 | Walt et al. |
| 5,250,439 A | 10/1993 | Musho et al. |
| 5,254,633 A | 10/1993 | Han et al. |
| 5,312,896 A | 5/1994 | Bhardwaj et al. |
| 5,323,309 A | 6/1994 | Taylor et al. |
| 5,364,797 A | 11/1994 | Olson et al. |
| 5,387,462 A | 2/1995 | Debe |
| 5,414,069 A | 5/1995 | Cumming et al. |
| 5,451,663 A | 9/1995 | Kang et al. |
| 5,451,683 A | 9/1995 | Barrett et al. |
| 5,493,017 A | 2/1996 | Therien et al. |
| 5,511,547 A | 4/1996 | Markle et al. |
| 5,512,490 A | 4/1996 | Walt et al. |
| 5,512,635 A | 4/1996 | Nubel et al. |
| 5,532,129 A | 7/1996 | Heller |
| 5,540,999 A | 7/1996 | Yamamoto et al. |
| 5,546,889 A | 8/1996 | Wakita et al. |
| 5,549,851 A | 8/1996 | Fukushima et al. |
| 5,554,747 A | 9/1996 | Sharma et al. |
| 5,556,524 A | 9/1996 | Albers |
| 5,563,056 A | 10/1996 | Swan et al. |
| 5,565,322 A | 10/1996 | Heller |
| 5,580,527 A | 12/1996 | Bell et al. |
| 5,585,646 A | 12/1996 | Kossovsky et al. |
| 5,591,787 A | 1/1997 | Schlennert et al. |
| 5,597,890 A | 1/1997 | Jenekhe |
| 5,607,864 A | 3/1997 | Ricchiero et al. |
| 5,629,353 A | 5/1997 | Steckle, Jr. et al. |
| 5,674,698 A | 10/1997 | Zarling et al. |
| 5,674,751 A | 10/1997 | Jaduszliwer et al. |
| 5,675,001 A | 10/1997 | Hoffman et al. |
| 5,679,773 A | 10/1997 | Holmes |
| 5,700,696 A | 12/1997 | Chandross et al. |
| 5,705,348 A | 1/1998 | Meade et al. |
| 5,709,994 A | 1/1998 | Pease et al. |
| 5,710,187 A | 1/1998 | Steckle, Jr. et al. |
| 5,710,197 A | 1/1998 | Fischer et al. |
| 5,723,218 A | 3/1998 | Haugland et al. |
| 5,858,907 A | 1/1999 | Wang et al. |
| 5,869,592 A | 2/1999 | Gagne et al. |
| 5,925,517 A | 7/1999 | Tyagi et al. |
| 5,942,638 A | 8/1999 | Lichtenhan et al. |
| 5,998,204 A | 12/1999 | Tsien et al. |
| 6,020,426 A | 2/2000 | Yamaguchi et al. |
| 6,124,421 A | 9/2000 | Lau et al. |
| 6,254,829 B1 | 7/2001 | Hartmann et al. |
| 6,259,277 B1 | 7/2001 | Tour et al. |
| 6,303,733 B1 | 10/2001 | Lau et al. |
| 6,323,309 B1 | 11/2001 | Swager et al. |
| 6,328,932 B1 | 12/2001 | Carter et al. |
| 6,444,476 B1 | 9/2002 | Morgan |
| 6,444,479 B1 | 9/2002 | Choi |
| 6,469,123 B1 | 10/2002 | Lau et al. |
| 6,509,110 B1 | 1/2003 | Salbeck et al. |
| 6,556,335 B2 | 4/2003 | Lee et al. |
| 6,589,731 B1 | 7/2003 | Chen et al. |
| 6,605,693 B1 | 8/2003 | Becker et al. |
| 6,610,848 B1 | 8/2003 | Pilato et al. |
| 6,660,820 B1 | 12/2003 | Martin et al. |
| 6,664,111 B2 | 12/2003 | Bentsen et al. |
| 6,670,645 B2 | 12/2003 | Grushin et al. |
| 6,713,298 B2 | 3/2004 | McDevitt et al. |
| 6,743,640 B2 | 6/2004 | Whitten et al. |
| 6,770,220 B1 | 8/2004 | Klimant |
| 6,783,814 B2 | 8/2004 | Swager et al. |
| 6,828,450 B2 | 12/2004 | Hua et al. |
| 6,830,828 B2 | 12/2004 | Thompson et al. |
| 6,835,835 B1 | 12/2004 | Huo |
| 6,902,830 B2 | 6/2005 | Thompson et al. |
| 6,919,139 B2 | 7/2005 | Grushin et al. |
| 6,946,688 B2 | 9/2005 | Grushin et al. |
| 6,962,757 B2 | 11/2005 | Epstein et al. |
| 7,001,536 B2 | 2/2006 | Thompson et al. |
| 7,029,765 B2 | 4/2006 | Kwong et al. |
| 7,041,910 B2 | 5/2006 | Swager et al. |
| 7,075,102 B2 | 7/2006 | Grushin et al. |
| 7,078,725 B2 | 7/2006 | Grushin et al. |
| 7,087,321 B2 | 8/2006 | Kwong et al. |
| 7,088,757 B1 | 8/2006 | Yu et al. |
| 7,098,060 B2 | 8/2006 | Yu et al. |
| 7,122,383 B2 | 10/2006 | Jones et al. |
| 7,129,518 B2 | 10/2006 | Grushin et al. |
| 7,186,355 B2 | 3/2007 | Swager |
| 7,208,122 B2 | 4/2007 | Swager et al. |
| 7,250,519 B2 | 7/2007 | Stossel et al. |
| 7,291,503 B2 | 11/2007 | Swager |
| 7,393,503 B2 | 7/2008 | Swager et al. |
| 7,417,146 B2 | 8/2008 | Huo |
| 7,462,325 B2 | 12/2008 | Hancock et al. |
| 7,521,232 B2 | 4/2009 | Moon |
| 7,662,309 B2 | 2/2010 | Swager et al. |
| 7,671,166 B2 | 3/2010 | Swager et al. |
| 7,759,127 B2 | 7/2010 | Rose et al. |
| 7,943,062 B2 | 5/2011 | Swager et al. |
| 8,158,437 B2 | 4/2012 | Swager et al. |
| 8,198,096 B2 | 6/2012 | Swager et al. |
| 8,283,423 B2 | 10/2012 | Swager et al. |
| 8,298,830 B2 | 10/2012 | Rose et al. |
| 8,367,001 B2 | 2/2013 | Swager et al. |
| 8,465,678 B2 | 6/2013 | Swager et al. |
| 8,617,819 B2 | 12/2013 | Swager et al. |
| 8,802,447 B2 | 8/2014 | Swager et al. |
| 2002/0040805 A1 | 4/2002 | Swager |
| 2002/0051985 A1 | 5/2002 | Whitten et al. |
| 2002/0076830 A1 | 6/2002 | Mauze et al. |
| 2002/0137978 A1 | 9/2002 | Grubbs et al. |
| 2002/0150697 A1 | 10/2002 | Swager et al. |
| 2002/0150759 A1 | 10/2002 | Jones et al. |
| 2002/0177136 A1 | 11/2002 | McBranch et al. |
| 2003/0054413 A1 | 3/2003 | Kumaraswamy et al. |
| 2003/0096138 A1 | 5/2003 | Lecloux et al. |
| 2003/0134959 A1 | 7/2003 | Hancock et al. |
| 2003/0178607 A1 | 9/2003 | Swager et al. |

(56) References Cited

U.S. PATENT DOCUMENTS

| | | |
|---|---|---|
| 2004/0043251 A1 | 3/2004 | Epstein et al. |
| 2004/0089867 A1 | 5/2004 | Grushin et al. |
| 2004/0094768 A1 | 5/2004 | Yu et al. |
| 2004/0094769 A1 | 5/2004 | Grushin et al. |
| 2004/0106741 A1 | 6/2004 | Kriesel et al. |
| 2004/0116650 A1 | 6/2004 | Swager et al. |
| 2004/0121337 A1 | 6/2004 | Deans et al. |
| 2004/0170775 A1 | 9/2004 | Swager et al. |
| 2004/0175768 A1 | 9/2004 | Kushon et al. |
| 2004/0188673 A1 | 9/2004 | Grushin et al. |
| 2004/0197602 A1 | 10/2004 | Dobbs et al. |
| 2004/0235184 A1 | 11/2004 | Swager |
| 2004/0241768 A1 | 12/2004 | Whitten et al. |
| 2004/0254388 A1 | 12/2004 | Spreitzer et al. |
| 2005/0014160 A1 | 1/2005 | Kumaraswamy et al. |
| 2005/0037232 A1 | 2/2005 | Tyan et al. |
| 2005/0054854 A1 | 3/2005 | Stossel et al. |
| 2005/0059168 A1 | 3/2005 | Bazan et al. |
| 2005/0147534 A1 | 7/2005 | Swager et al. |
| 2005/0157261 A1 | 7/2005 | Hanebuchi et al. |
| 2005/0176624 A1 | 8/2005 | Thompson et al. |
| 2005/0186447 A1 | 8/2005 | Grushin et al. |
| 2005/0196775 A1 | 9/2005 | Swager et al. |
| 2005/0220714 A1 | 10/2005 | Kauzlarich et al. |
| 2005/0226775 A1 | 10/2005 | Aker et al. |
| 2005/0263758 A1 | 12/2005 | Treacher et al. |
| 2005/0285517 A1 | 12/2005 | Yu et al. |
| 2006/0024707 A1 | 2/2006 | Deans et al. |
| 2006/0029829 A1 | 2/2006 | Thompson et al. |
| 2006/0057425 A1 | 3/2006 | Grushin et al. |
| 2006/0058524 A1 | 3/2006 | Falcou et al. |
| 2006/0073607 A1 | 4/2006 | Rose et al. |
| 2006/0120917 A1 | 6/2006 | Swager et al. |
| 2006/0127929 A1 | 6/2006 | Swager et al. |
| 2006/0135772 A1 | 6/2006 | Huo |
| 2006/0173145 A1 | 8/2006 | Pawlow et al. |
| 2006/0270846 A1 | 11/2006 | Karpishin et al. |
| 2007/0081921 A1 | 4/2007 | Swager et al. |
| 2007/0083066 A1 | 4/2007 | Bohm et al. |
| 2008/0085566 A1 | 4/2008 | Swager et al. |
| 2009/0215189 A1 | 8/2009 | Swager et al. |
| 2010/0063225 A1 | 3/2010 | Swager et al. |
| 2010/0112715 A1 | 5/2010 | Swager et al. |
| 2010/0168352 A1 | 7/2010 | Arriola et al. |
| 2010/0213451 A1 | 8/2010 | Swager et al. |
| 2010/0310424 A1 | 12/2010 | Rose et al. |
| 2011/0142717 A1 | 6/2011 | Swager et al. |
| 2011/0175035 A1 | 7/2011 | Swager et al. |
| 2015/0031138 A1 | 1/2015 | Swager et al. |

FOREIGN PATENT DOCUMENTS

| | | |
|---|---|---|
| DE | 198 06 037 A1 | 9/1999 |
| EP | 0 259 951 A2 | 3/1988 |
| EP | 0 442 123 A1 | 8/1991 |
| EP | 0 581 058 A1 | 2/1994 |
| EP | 0 748 805 | 12/1996 |
| EP | 1 011 154 A1 | 6/2000 |
| JP | 06-322078 | 11/1994 |
| WO | WO 89/00593 | 1/1989 |
| WO | WO 95/16681 | 6/1995 |
| WO | WO 98/05693 | 2/1998 |
| WO | WO 99/19419 | 4/1999 |
| WO | WO 99/57222 | 11/1999 |
| WO | WO 00/05774 | 2/2000 |
| WO | WO 00/53655 A1 | 9/2000 |
| WO | WO 01/57140 A1 | 8/2001 |
| WO | WO 02/16463 A2 | 2/2002 |
| WO | WO 02/074997 | 9/2002 |
| WO | WO 02/079268 A2 | 10/2002 |
| WO | WO 03/048226 A2 | 6/2003 |
| WO | WO 2004/057014 A2 | 7/2004 |
| WO | WO 2005/030681 A1 | 4/2005 |
| WO | WO 2005/086617 A2 | 9/2005 |
| WO | WO 2006/081345 A1 | 8/2006 |
| WO | WO 2006/085319 A2 | 8/2006 |
| WO | WO 2008/019086 | 2/2008 |
| WO | WO 2008/039529 | 4/2008 |
| WO | WO 2008/042289 | 4/2008 |
| WO | WO 2008/136805 | 11/2008 |

OTHER PUBLICATIONS

[No Author Listed] Institute for Soldier Nanotechnologies. Downloaded from http://web.mit.edu/isn/industryday/index.html on Jan. 30, 2003.

Abraham et al., "Hydrogen bonding. Part 29. Characterization of 14 Sorbent Coatings for Chemical Microsensors using a New Solvation Equation," J. Chem. Soc. Perkin Trans. 1995, 2, 369-378.

Achyuthan, Ke, et al., "Fluorescence superquenching of conjugated polyelectrolytes: applications for biosensing and drug discovery", Journal of Materials Chemistry, vol. 15 (27-28): 2648-2656, (2005).

Albert et al., Designing optical sensor arrays with enhanced sensitivity for explosives detection. Proceeedings of the SPIE—The International Society for Optical Engineering. Orlando, Florida. Apr. 13-17, 1998;3392(1-2):426-31. Abstract Only.

Amara et al., "Synthesis and Properties of Poly(phenylene ethynylene)s with Pendant Hexafluoro-2-propanol Groups," Macromolecules 2005, 38, 9091-9094.

Amara, J. et al., "Incorporation of Internal Free Volume: Synthesis and Characterization of Iptycene-Elaborated Poly(butadiene)s," Macromolecules 2004, 37, 3068-3070.

Arias-Marin et al., Amphiphilic Phenyl—Ethynylene Polymers and Copolymers. Synthesis, Characterization, and Optical Emission Properties. Macromolecules. 2003;36:3570-79.

Armengaud et al., "Electrochemistry of conducting polypyrrole films containing cobalt porphyrin," J. Electroanal. Chem., 1990, 277:197-211.

Audebert et al., "Description of New Redox and Conducting Polymers Based on Copper Containing Units; Emphasis on the Role of Copper in the Electron Transfer Mechanism," Synthetic Metals, 1991, 3049-3052.

Audebert et al., "Redox and Conducting Polymers Based on Salen-Type Metal Units; Electrochemical Study and Some Characteristics," New Journal of Chemistry, 1992 16(6):697-703.

Audebert et al., "Synthesis and Characteristics of New Redox Polymers Based on Copper Containing Units; Evidence for the Participation of Copper in the Electron Transfer Mechanism," New Journal of Chemistry, 1991, 15(4):235-237.

Baldo et al., "Excitonic singlet-triplet ratio in a semiconducting organic thin film," Phys. Rev. B., 1999, 60(20), 14422-14428.

Baldo et al., "High-efficiency fluorescent organic light-emitting devices using a phosphorescent sensitizer," Nature, 2000, 403, 750-753.

Barigelletti et al., "Temperature Dependence of the Luminescence of Cyclometalated Palladium(II), Rhodium(III), Platinum(II), and Platinum(IV) Complexes," Inorg. Chem. 1988, 27, 3644-47.

Bedioui et al., "Electrochemistry of conducting polypyrrole films containing cobalt porphyrin, Part 2. New Developments and inclusion of metallic aggregates in the coordination polymer," J. Electroanal. Chem., 1991, 297:257-269.

Bedioui et al., "Electrooxidative polymerization of cobalt, nickel and manganese salen complexes in acetonitrile solution," J. Electroanal. Chem., 1991, 301:267-274.

Bedioui et al., "Poly(Pyrrole-Manganese Tetraphenylporphyrin) film Electrodes in Acetonitrile Solution," J. Electroanal. Chem., 1988, 239:433-439.

Bergstedt, T, et al., "Superquenching of fluorescent polyelectrolytes and its applications for chemical and biological sensing," in Organic Photonic Materials and Devices III, Bernard Kippelen, Donal D. C. Bradley, Editors, Proceedings of SPIE vol. 4279, 94-100 (2001).

Bettelheim et al., "Electrochemical Polymerization of Amino-, Pyrrole-, and Hydroxy- Substituted Tetraphenylporphyrins," Inorganic Chemistry, 1987, 26(7):1009-1017.

Bowyer et al., Electrochemical reduction of vicinal dinitro compounds. J Org Chem. 1988;53(22):5234-5239.

Brabec, Christoph, et al. "Plastic Solar Cells", Adv. Funct. Mater, 2001, vol. 11, No. 1, pp. 15-26.

(56) References Cited

OTHER PUBLICATIONS

Bredas et al., "Electronic Structure of Poly(paraphenylene vinylene): Influence of Copolymerization and Derivatization on Light-Emitting Characteristics," Am. Chem. Scoc., Div. Polym. Chem., 1994, 35, 185-186.
Brooks et al., "Synthesis and Characterization of Phosophorescent Cyclometalated Platinum Complexes," Inorg. Chem., 2002, 41(12), 3055-3066.
Brown et al., "Core-referenced ratiometric fluorescent potassium ion sensors using self-assembled ultrathin films on europium nanoparticles," IEEE Sensors Journal, 2005, 5(6), 1197-1205.
Brown et al., Fluorescence-enhancement sensing of ammonia and hydrazines via disruption of the internal hydrogen bond in a carbazolopyridinophane. Sensors Actuators B. 2005;110:8-12.
Bustin, Absolute quantification of mRNA using real-time reverse transcription polymerase chain reaction assays. J Mol Endocrinol. Oct. 2000;25(2):169-93.
Cabarcos et al., "Effect of the Molecular Weight and the Ionic Strength on the Photoluminescence Quenching of Water-Soluble Conjugated Polymer Sodium Poly[2-(3-thienyl)ethyloxy-4-butylsulfonate]," Macromolecules, 2005, 38(25), 10537-10541.
Cameron et al., "A conjugated polymer/redox polymer hybrid with electronic communication between metal centres," Chem. Commun., 1997, 303-304.
Carrabba et al., Hydrogen bonding in the lowest singlet n-pi-star excited state of pyrimidine. J Phys Chem. 1985;89:674-77.
Chassot et al., "cis-Bis(2-phenylpyridine platinum(II)(CBPPP): A Simple Molecular Platinum Compound," Inorg. Chem., 1984, 23(25), 4249-4253.
Chassot et al., "Cyclometalated Complexes of Platinum(II): Homoleptic Compounds with Aromatic C,N Ligands," Inorg. Chem., 1987, 26(17), 2814-2818.
Chassot et al., "Photochemical Preparation of Luminsecent Platinum(IV) Complexes via Oxidative Addition on Luminescent Platinum(II) Complexes," J. Am. Chem. Soc., 1986, 108, 6084-6085.
Chatterjee et al.,Synthesis of Functionalized Olefins by Cross and Ring-Closing Metatheses. J Am Chem Soc. 2000;122(15):3783-84.
Chen, L., et al., "Surfactant-Induced Modification of Quenching of Conjugated Polymer Fluorescence by Electron Acceptors: Applications for Chemical Sensing," Chem. Phys. Lett. 330 (1-2) (2000) pp. 27-33.
Chen, Liaohai et al., "Tuning the properties of conjugated polyelectrolytes through surfactant complexation," J. Am. Chem. Soc., 2000, vol. 122 No. 38, pp. 9302-9303.
Chen, Liaohai, et al., "Highly sensitive biological and chemical sensors based on reversible fluorescence quenching in a conjugated polymer," PNAS, Oct. 26, 1999, vol. 96 No. 22, 12287-12292.
Choi et al, Oxygen-sensitive reverse-phase optode membrane using silica gel-absorbed ruthenium(II) complex embedded in gelatin film. Anal. Chim. Acta 1999, 387, 197-205.
Costa-Fernandez et al., "Sol-gel immobilized room-temperature phosphorescent metal-chelate as luminescent oxygen sensing material," *Anal. Chim. Acta.*, 1998, 360, 17-26.
Cotts, Patricia M., et al., "Equilibrium Flexibility of a Rigid Linear Conjugated Polymer," Macromolecules, 1996, vol. 29, pp. 7323-7328.
Cumming et al., "Using Novel Fluorescent Polymers as Sensory Materials for Above-Ground Sensing of Chemical Signature Compounds Emanating from Buried Landmines," IEEE Transactions on Geoscience and Remote Sensing, 2001, 39:1119-1128.
Dagani, Ron, "A Better Sensor for Nerve Gas," C&EN, Mar. 10, 2003, p. 12.
Dahm et al., "Catalytic Reduction of Iodoethane and 2-Iodopropane at Carbon Electrodes Coated with Anodically Polymerized Films of Nickel(II) Salen," Analytical Chemistry, 1994, 66(19):3117-3123.
Dai et al., Sensors and sensor arrays based on conjugated polymers and carbon nanotubes. Pure Appl Chem. 2002;74(9):1753-72.

Davey et al., New Rigid Backbone Conjugated Organic Polymers with Large Fluorescence Quantum Yields. J Chem Soc Chem Commun. 1995;1433-34.
Deans, Robert, et al., "A Poly(p-phenyleneethynylene) with a Highly Emissive Aggregated Phase", J. Am. Chem. Soc., 2000, vol. 122, pp. 8565-8566.
Decher, "Fuzzy Nanoassemblies: Toward Layered Polymeric Multicomposites," Science, 1997, 277(5330), 1232-1237.
Demchenko et al., "The problem of self-calibration of fluorescence signal in microscale sensor systems," Lab on a Chip, 2005, 5, 1210-1223.
Deng et al., "Direct Observation of the "Pac-Man" Effect from Dibenzofuran-Bridged Cofacial Bisporphyrins," J. Am. Chem. Soc. 2000, 122, 410-411.
Dijkstra et al., "Shape-Persistent Nanosize Organometallic Complexes: Synthesis and Application in a Nanofiltration Membrane Reactor," J. Org. Chem., 2003, vol. 68, No. 3, pp. 675-685.
Disney, M.D. et al., "Detection of Bacteria with Carbohydrate-Functionalized Fluorescent Polymers," J. Am. Chem. Soc. 2004, 126, 13343-13346.
Dougherty et al., "Photodynamic Therapy," J. Natl. Cancer Inst., 1998, 90(12), 889-905.
Dudek et al., Synthesis and energy-transfer properties of hydrogen-bonded oligofluorenes. J Am Chem Soc. Aug. 24, 2005;127(33):11763-8.
Dwight et al., "Perturbation of Fluorescence by Nonspecific Interactions between Anionic Poly(phenylenevinylene)s and Proteins: Implications for Biosensors," J. Am. Chem. Soc., 2004, 126(51), 16850-16859.
Ellis et al., Conductive Polymer Films as Ultrasensitive Chemical Sensors for Hydrazine and Monomethylhydrazine Vapor. Anal Chem. 1996;68:817-22.
Erdogan et al., Synthesis and mesoscopic order of a sugar-coated poly(p-phenyleneethynylene). Macromolecules. 2002;35:7863-64.
Ewing et al., Detection of volatile vapors emitted from explosives with a handheld ion mobility spectrometer. Field Anal Chem Technol. 2001;5:215-21.
Famulok et al., Nucleic acid aptamers-from selection in vitro to applications in vivo. Acc Chem Res. Sep. 2000;33(9):591-9.
Fan, C, et al., "High-Efficiency Fluorescence Quenching of Conjugated Polymers by Proteins," J. Am. Chem Soc., 2002, 124(20): pp. 5642-5643.
Fan, C, et al., "Photoluminescence Quenchers of Water Soluble Conjugated Polymers by Viologen Derivatives: Effect of Hydrophobicity," Langmuir, 2003, 19(8): pp. 3554-3556.
Fan, C, S., et al, "Beyond superquenching: Hyper-efficient energy transfer from conjugated polymers to gold nanoparticles," PNAS, 2003, 100(11): pp. 6297-6301.
Fiesel, Rainer, et al., "A chiral poly(para-phenyleneethynylene) (PPE) derivative," Macromol. Rapid Commun., 1998, vol. 19, No. 8, pp. 427-431.
Fiesel, Rainer, et al., "Aggregation-induced CD effects in chiral poly(2,5-dialkoxy-1,4-phenylene)s," Acta Polym., 1998, vol. 49, pp. 445-449.
Fiesel, Rainer, et al., "On the Solid State Aggregation of Chiral Substituted Poly(para-phenylene)s (PPPs)," Synthetic Metals, 1999, vol. 102, pp. 1457-1458.
Fu, Dian-Kui, et al., "Alternating Poly(PyridylVinylenePhenyleneVinylene)s: Synthesis and Solid State Organizations," Tetrahedron, 1997, vol. 53, No. 45, pp. 15487-15494.
Funhoff et al., Cationic polymethacrylates with covalently linked membrane destabilizing peptides as gene delivery vectors. J Control Release. Jan. 3, 2005;101(1-3):233-46.
Garner, C., et al., "Challenges for dielectric materials in future integrated circuit technologies," Microelectronics Reliability 2005, 45, 919-924.
Gaylord, B.S, et al., "DNA Hybridization Detection with Water-Soluble Conjugated Polymers and Chromophore-Labeled Single Stranded DNA," J. Am. Chem Soc., 2003, 125(4): pp. 896-900.
Gaylord, B.S., et al., "Water-Soluble Conjugated Oligomers: Effect of Chain Length and Aggregation on Photoluminescence-Quenching Efficiencies," J. Am. Chem. Soc. 2001, 123(26): 6417-6418.

(56) References Cited

OTHER PUBLICATIONS

Gaylord, B.S., et al., "SNP detection using peptide nucleic acid probes and conjugated polymers: Applications in neurodegenerative disease identification," PNAS, vol. 102, No. 1, pp. 34-39 (2005).
Gaylord, Brent S., et al., "DNA detection using water-soluble conjugated polymers and peptide nucleic acid probes," PNAS, Aug. 20, 2002, vol. 99, No. 17, pp. 10954-10957.
Gianini et al., "Chiral Cyclometalated Platinum(II) Complexes with Derivatives of Thienylpyridine as Ligands: Helical Distortion of the Square Planar (SP-4) Geometry," Inorg. Chem, 1997, 36(26), 6094-6098.
Gianini et al., "Square Planar (SP-4) and Octahedral (OC-6) Complexes of Platinum (II) and —(IV) with Predetermined Chirality at the Metal Center," Inorg. Chem., 1996, 35(17), 4889-4895.
Goldfinger et al., "Fused polycyclic aromatics via electrophile-induced cyclization reactions: application to the synthesis of graphite ribbons", J. Am. Chem. Soc., 1994, vol. 116, pp. 7895-7896.
Goldsby et al., "Oxidation of Nickel(II) Bis(salicylaldimine) Complexes: Solvent Control of the Ultimate Redox Site," Polyhedron, 1989, 8(1):113-115.
Goldsby et al., "Symmetric and Unsymmetric Nickel(II) Schiff Base Complexes; Metal-Localized Versus Ligand-Localized Oxidation," J. Coord. Chem., 1988, 19:83-90.
Grate et al., "Hydrogen Bond Acidic Polymers for Surface Acoustic Wave Vapor Sensors and Arrays," Anal. Chem. 1999, 71, 1033-1040.
Grate, "Acoustic Wave Microsensor Arrays for Vapor Sensing," Chem Rev. 2000, 100, 2627-2647.
Guice et al., "Nanoscale internally referenced oxygen sensors produced from self-assembled nanofilms on fluorescent nanoparticles," Journal of Biomedical Optics, 2005, 10(6), 064031-1-064031-10.
Guimaraes et al., On the fluoresence of pyrrole derivative oligomer. Mater Sci Engineer C. 2008;28:1076-81.
Halkyard, Carrie E., et al., "Evidence of Aggregate Formation for 2,5-Dialkylpoly (p-phenyleneethynylenes) in Solution and Thin Films," Macromolecules, Nov. 25, 1998, vol. 31, No. 25, pp. 8655-8659.
Hard et al., Fluorescence studies of a single tyrosine in a type II DNA binding protein. Biochemistry. Jan. 10, 1989;28(1):396-406.
Harrison, Benjamin S., et al., "Amplified Fluorescence Quenching in a Poly(p-phenylene)-Based Cationic Polyelectrolyte," J. Am. Chem. Soc., Aug. 16, 2001, vol. 122, No. 35, pp. 8561-8562.
Havemann, R., "High-Performance Interconnects: An Integration Overview," Proceedings of the IEEE 2001, 89(5), 586-601.
Heeger, P., et al., "Making sense of polymer-based biosensors," PNAS, vol. 96, No. 22, pp. 12219-12221 (1999).
Herbich et al. "Fluorescence Quenching by Pyridine and Derivatives Induced by Intermolecular Hydrogen Bonding to Pyrrole-Containing Heteroaromatics," J. Phys. Chem. A. 2002, 106, 2158-2163.
Hill et al., "A Mechanistic Study of the Photochemically Initiated Oxidative Addition of Isopropyl Iodide to Dimethl(1,10-phenanthroline)platinum(II),"J. Am. Chem. Soc., 1985, 107(5), 1218-1225.
Hoferkamp et al., "Surface-Modified Electrodes Based on Nickel(II) and Copper(II) Bis(salicylaldimine) Complexes," Chemistry of Materials, 1989, 1(3):348-352.
Hoffmeister et al., "Triptycene Polymers," J. Polymer Science 1969, 7, 55-72.
Höger, Sigurd, et al., "Synthesis, Aggregation, and Adsorption Phenomena of Shape-Persistent Macrocycles with Extraannular Polyalkuly Substituents," J. Am. Chem. Soc., May 22, 2001, vol. 123, No. 24, pp. 5651-5659.
Horwitz et al., "Oxidative Electropolymerization of Metal Schiff-Base Complexes," Mol. Cryst. Liq. Cryst., 1988, 160:389-404.
Houk et al., "[C-H• • •O] Interactions as a Control Element in Supramolecular Complexes: Experimental and Theoretical Evaluation of Receptor Affinities for the Binding of Bipyridinium-Based Guests by Catenated Hosts," J. Am. Chem. Soc., 1999, 121(7), 1479-1487.
Houser et al.. Rational materials design of sorbent coatings for explosives: applications with chemical sensors. Talanta. May 10, 2001;54(3):469-85.
Huang et al., "Design of a Modular-Based Fluorescent Conjugated Polymer for Selective Sensing," Angew. Chem. Int. Ed., 2004, 43(42), 5635-5638.
Huang et al., Nanostructured polyaniline sensors. Chem Euro J. Mar. 19, 2004;10(6):1314-9.
Jayarajah et al., "Oxygen Diffusion and Permeability in Alkylaminothionylphosphazene Films Intended for Phosphorescence Barometry Applications," Macromolecules, 2000, 33(15), 5693-5701.
Jensen et al., Cytoplasmic delivery and nuclear targeting of synthetic macromolecules. J Control Release. Feb. 21, 2003;87(1-3):89-105.
Jolliet et al., "Cyclometalated Complexes of Palladium(II) and Platinum(II): cis-Configured Homoleptic and Heteroleptic Compounds with Aromatic C^N Ligands," Inorg. Chem., 1996, 35(17), 4883-4888.
Joly et al., "Highly Effective Water-Soluble Fluorescence Quenchers of Conjugated Polymer Thin Films in Aqueous Environments," Macromolecules, 2006, 39(21), 7175-7177.
Jones, R.M., et al., "Building highly sensitive dye assemblies for biosensing from molecular building blocks," PNAS USA 2001, 98(26): 14769-14772.
Jones, R.M., et al., "Superquenching and Its Applications in J-Aggregated Cyanine Polymers," Langmuir, 2001, 17, 2568-2571.
Jones, R.M., et al., "Tuning of Superquenching in Layered and Mixed Fluorescent Polyelectrolytes," J. Am. Chem. Soc. 2001, 123: 6726-6727.
Katayama et al., Vinylideneruthenium complexes in catalysis. Coord Chem Revs. 2004;248:1703-15.
Kim et al. "Nonspecific Interactions of a Carboxylate-Substituted PPE with Proteins. A Cautionary Tale for Biosensor Applications," Langmuir, 2005, 21(17), 7985-7989.
Kim et al., "Control of conformational and interpolymer effects in conjugated polymers," Nature, 2001, 411, 1030-1034.
Kim et al., "Directing Energy Transfer within Conjugated Polymer Thin Films," J. Am. Chem. Soc., 2001, 123(46), 11488-11489.
Kim et al., "Ion-Specific Aggregation in Conjugated Polymers: Highly Sensitive and Selective Fluorescent Ion Chemosensors," Agnew Chem. Int. Ed., 2000, 39(21), 3868-3872.
Kim et al., "Nanoscale Fibrils and Grids: Aggregated Structures from Rigid-Rod Conjugated Polymers," Macromolecules, 1999, 32 (5), 1500-1507.
Kim et al., "Structural Control in Thin Layers of Poly)P-phenyleneethynylene)s: Photophysical Studies of Langmuir and Langmuir-Blodgett Films," J. Am. Chem. Soc., 2002, 124(26), 7710-7718.
Kim et al., "Ultrafast Energy-Transfer Dynamics between Block Copolymer and n-Conjugated Polymer Chains in Blended Polymeric Systems," Chemistry of Materials, 13(8), 2666-2674, (2001).
Kim, T.-H. et al. "A Fluorescent Self-Amplifying Wavelength Responsive Sensory Polymer for Fluoride Ion," Angew. Chem. Int. Ed. 2003, 42, 4803-4806.
Köhler, Bernhard, et al., "Novel Chiral Macrocycles Containing Two Electronically Interacting Arylene Chromophores," Chem. Eur. J., 2001, vol. 7, No. 14, pp. 3000-3004.
Kraft, Arno, et al., "Electroluminescent Conjugated Polymers—Seeing Polymers in a New Light," Agnew. Chem. Int. Ed. 1998, 37, 402-428.
Kui et al., "Structures, Photoluminescence, and Reversible Vapoluminescence Properties of Neutral Platinum(II) Complexes Containing Extended p-Conjugated Cyclometalated Ligands," J. Am. Chem. Soc. 2006, 128, 8297-309.
Kumaraswamy, S., et al., "Fluorescent-conjugated polymer superquenching facilitates highly sensitive detection of proteases," PNAS, May 18, 2004, 101(20): pp. 7511-7515.

(56) References Cited

OTHER PUBLICATIONS

Kushon, S.A., et al., "Detection of DNA Hybridization via Fluorescent Polymer Superquenching," Langmuir, 2002, 18(20): pp. 7245-7249.

Kushon, S.A., et al., "Detection of single nucleotide mismatches via fluorescent polymer superquenching," Langmuir, 2003, 19(20): pp. 6456-6464.

Lamansky et al., "Highly Phosphorescent Bis-Cyclometalated Iridium Complexes: Synthesis, Photophysical Characterization, and Use in Organic Light Emitting Diodes," J. Am. Chem. Soc., 2001, 123(18), 4304-4312.

Lamba et al., "Imine-Bridged Planar Poly(p-phenylene) Derivatives for Maximization of Extended π-Conjugation. The Common Intermediate Approach," J. Am. Chem. Soc., 1994, 116(26), 11723-11736.

Langeveld-Voss, B.M.W., et al., "Circular Dichroism and Circular Polarization of Photoluminescence of Highly Ordered Poly{3,4-di[(S)-2-methylbutoxy{thiophene}," J. Am. Chem. Soc., 1996, vol. 118, No. 20, pp. 4908-4909.

Levitsky, et al., "Rational Design of a Nile Red/Polymer Composite Film for Fluorescence Sensing of Organophosphonate Vapors Using Hydrogen Bond Acidic Polymers," Anal. Chem. 2001, 73, 3441-3448.

Levitsky, et al., "Signal Amplification in Multichromophore Luminescence-Based Sensors," J. Phys. Chem. B, 2001, 105, 8468-8473.

Levitsky, Igor A., et al., "Energy Migration in a Poly(phenylene ethynylene): Determination of Interpolymer Transport in Anisotropic Langmuir-Blodgett Films," J. Am. Chem. Soc., 1999, vol. 121, No. 7, pp. 1466-1472.

Levitsky, Igor A., et al., "Mass and Energy Transport in Conjugated Polymer Langmuir-Blodgett Films; Conductivity, Fluorescence, and UV-Vis Studies," Macromolecules, Mar. 27, 2001, vol. 34, No. 7, pp. 2315-2319.

Li et al., Water-Soluble Poly(acrylic acid) Grafted Luminescent Silicon Nanoparticles and Their Use as Fluorescent Biological Staining Labels. Nano Letters. 2004; 4(8):1463-1467.

Li, Mei, et al., "Novel Surfactant-Free Stable Colloidal Nanoparticles Made of Randomly Carboxylated Polystyrene Ionomers," Macromolecules, 1997, vol. 30, No. 7, pp. 2201-2203.

Liao et al., "Quantification of Amplified Quenching for Conjugated Polymer Microsphere Systems," Langmuir, 2007, 23(1), 112-115.

Lim et al., Transferrin-oligomers as potential carriers in anticancer drug delivery. Pharm Res. Nov. 2004;21(11):1985-92.

Lipkowitz et al., A protocol for determining enantioselective binding of chiral analytes on chiral chromatographic surfaces. J Am Chem Soc. 1988;110:3446-52.

Liu et al., "Fluorescence Quenching Mechanism of a Polyphenylene Polyelectrolyte with Other Macromolecules: Cytochrome c and Dendrimers," Langmuir, 2005, 21(5), 1687-1690.

Liu, B., et al., "Homogeneous Fluorescence-Based DNA Detection with Water-Soluble Conjugated Polymers," Chem. Matter, vol. 16, pp. 4467-4476 (2004).

Liu, B., et al., "Methods for strand-specific DNA detection with cationic conjugated polymers suitable for incorporation into DNA chips and microarrays," PNAS, vol. 102, No. 3, pp. 589-593 (2005).

Liu, B., et al., "Optimization of the Molecular Orbital Energies of Conjugated Polymers for Optical Amplification of Fluorescent Sensors," J. Am. Chem. Soc., vol. 138, pp. 1188-1196 (2006).

Liu, et al., "Effect of Chromophore-Charge Distance on the Energy Transfer Properties of Water-Soluble Conjugated Oligomers," J. Am. Chem. Soc., vol. 125, pp. 6705-6714 (2003).

Long, T. et al., "Molecular Design of Free Volume as a Route to Low-κ Dielectric Materials," J. Am. Chem. Soc. 2003, 125, 14113-14119.

Lu L., et al., "Biocidal activity of a light-absorbing fluorescent conjugated polyelectrolyte", Langmuir, 2005 vol. 21, No. 22, pp. 10154-10159.

Lu, L., et al., "Cyanine pendant polymers on nanoparticles and in solution: superquenching and sensing applications," Polymeric Materials Science and Engineering, 2002, 86: pp. 17-18.

Lu, L., et al., "Self-assembled 'polymers' on nanoparticles: superquenching and sensing applications," Polymer Preprints (American Chemical Society, Division of Polymer Chemistry), 2002, 43: pp. 124-125.

Lu, L., et al., "Superquenching in cyanine pendant poly-L-lysine dyes: dependence on molecular weight, solvent and aggregation," Journal of the American Chemical Society, 2002, 124: pp. 483-488.

Lu, L., et al., "Surface-Enhanced Superquenching of Cyanine Dyes as J-Aggregates on Laponite Clay Nanoparticles," Langmuir, 2002, 18(20): pp. 7706-7713.

Luo, Laibin, et al., "Thermodynamic Stabilization Mechanism of Block Copolymer Vesicles," J. Am. Chem. Soc., 2001, vol. 123, No. 5, pp. 1012-1013.

MacDiarmid, Polyanaline and polypyrrole: Where are we headed? Synthetic Metals. 1997;84:27-34.

Maestri et al., "Absorption Spectra and Luminescence Properties of Isomeric Platinum(II) and Palladium(II) Complexes Containing 1,1'-Biphenyldiyl, 2-Phenylpyridine, and 2, 2'-Bipyridine as Ligands," Helvetica Chimica Acta 1988, 71, 1053-59.

Maex, K. et al., "Low dielectric constant materials for microelectronics," Journal of Applied Physics 2003, 93(11), 8793-841.

Maier, G., "Low dielectric constant polymers for microelectronics," Prog. Polym. Sci. 2001, 26, 3-65.

Manes et al., Extraction-spectrophotometric determination of hydrazine with 2-hydroxy-1-naphthaldehyde. Analyst. 1987;112:1183-84.

Martin, et al., "Picosecond Laser Photolysis Studies of Deactivation Processes of Excited Hydrogen-Bonding Complexes. 2. Dibenxocarbazole-Pyridine Systems," J. Phys. Chem. 1982, 86, 4148-4156.

Martin, S. et al., "Development of a Low-Dielectric-Constant Polymer for the Fabrication of Integrated Circuit Interconnect," Adv. Mater. 2000, 12(23), 1769-78.

Matloka et al., The acyclic diene metatheis (ADMET) polymerization approach to silicon containing materials. J Mol Catalysis. 2006;257:89-98.

McGill, et al., "Choosing polymer coatings for chemical sensors," Chemtech 1994, 24, 27-37.

McQquade, D. Tyler, et al., "Conjugated Polymer-Based Chemical Sensors," Chem. Rev., 2000, vol. 100, No. 7, pp. 2537-2574.

McQuade, D. tyler, et al., "Two-Dimensional Conjugated Polymer Assemblies: Interchain Spacing for Control of Photophysics," J. Am. Chem. Soc., 2000, vol. 122, No. 24, pp. 5885-5886.

Medintz et al., "Quantum dot bioconjugates for imaging, labelling and sensing," Nature Materials, 2005, 4(6), 435-446.

Miao, Yi-Jun, et al., "Fluorescence Sensory Polymers Containing Rigid Non-planar Aromatic Scaffolds," Proceedings of the 1997 Boston meeting, vol. 39, No. 2, pp. 1081-1082, Aug. 23-27, 1998, Polym. Prepr. Div. Polym. Chem. Am .Chem .Soc.; Polymer Preprints, Division of Polymer Chemistry, American Chemical Society, Aug. 1998 ACS, Washington D.C.

Mitschke, Ullrich et al., "The electroluminescence of organic materials," J. Mater. Chem., 2000, vol. 10, pp. 1471-1507.

Miyasaka, et al., "Femtosecond-Picosecond Laser Photolysis Studies on the Mechanisms of Fluorescence Quenching Induced by Hydrogen-Bonding Interactions—1-Pyrenol-Pyridine Systems," J. Phys. Chem. 1993, 97, 8222-8228.

Moisy et al., "Epoxidation of cis-cyclooctene by Molecular Oxygen Electrocatalysed by Polypyrrole-Manganese Porphyrin Film Modified Electrodes," J. Electroanal. Chem., 1988, 250:191-199.

Moon et al., Live-cell-permeable poly(p-phenylene ethynylene). Angew Chem Int Ed Engl. 2007;46(43):8223-5.

Moon, Joong Ho, et al., "Capture and detection of a quencher labeled oligonucleotide by poly)phenylene ethynylene) particles," Chem. Commun., Jan. 2003, vol. 1, pp. 104-105.

Morgen, M., et al., "Low Dielectric Constant Materials for ULSI Interconnects," Annu. Rev. Mater. Sci. 2000, 30, 645-80.

Morin et al., "Syntheses of Conjugated Polymers Derived from N-Alkyl-2,7-carbazoles," Macromolecules, 2001, 34(14), 4680-4682.

(56) References Cited

OTHER PUBLICATIONS

Moroni et al., Rigid Rod Conjugated Polymers for Nonlinear Optics. 3. Intramolecular H Bond Effects on Poly(phenyleneethynylene) Chains. Macromolecules. 1997;30:1964-72.
Murarka, S., "Materials aspects of copper interconnection technology for semiconductor applications," Materials Science and Technology 2001, 17, 749-58.
Ng et al., Syntheses and characterisation of electrically conductive and fluorescent poly[3-(ω-bromoalkyl)thiophenes]. Synthetic Metals. 1999;100:269-77.
Nie et al., "Immobilization of polydiacetylene onto silica microbeads for colorimetric detection," J. Mater. Chem., 2006, 16, 546-549.
Norvez, S., et al., "Epitaxygens: mesomorphic properties of triptycene derivatives," Liquid Chemicals, 1993, vol. 14, No. 5, pp. 1389-1395.
Oda, Masao, et al., "Chiroptical properties of chiral-substituted polyfluorenes," Synthetic Metals, 2000, vol. 111-112, pp. 575-577.
Oda, Masao, et al., "Circularly Polarized Electroluminescence from Liquid-Crystalline Chiral Polyfluorenes," Advanced Materials, 2000, vol. 12, No. 5, pp. 362-365.
Okamoto, I. et al., "Orbital Unsymmetrization Affects Facial Selectivities of Diels-Alder Dienophiles," J. Org. Chem. 1996, 61, 3155-3166.
Ortega-Barrales et al., Solid-phase spectrophotometric determination of trace amounts of hydrazine at sub-ng ml-1 level. Anal Chim Acta. 1997;353:115-22.
Orynbayeva et al., Visualization of membrane processes in living cells by surface-attached chromatic polymer patches. Angew Chem Int Ed Engl. Feb. 4, 2005;44(7):1092-6.
Osborne et al., Nucleic Acid Selection and the Challenge of Combinatorial Chemistry. Chem Rev. Apr. 1, 1997;97(2):349-370.
Ow et al., "Bright and stable core-shell fluorescent silica nanoparticles," Nano Letters, 2005, 5(1), 113-117.
Park et al., "Ratiometric Optical PEBBLE Nanosensors for Real-Time Magnesium Ion Concentrations Inside Viable Cells," Anal. Chem., 2003, 75(15), 3784-3791.
Patel, et al., "Chemicapacitive microsensors for volatile organic compound detection," Sensors and Actuators B, 2003, 96, 541-553.
Peeters, Emiel, et al., "Circularly Polarized Electroluminescence from a Polymer Light-Emitting Diode," J. Am. Chem. Soc., 1997, vol. 119, No. 41, pp. 9909-9910.
Pei et al., First Hydrogen-Bonding-Induced Self-Assembled Aggregates of a Polyfluorene Derivative. Macromolecules. 2003;36:323-27.
Pei et al., Polymer Light-Emitting Electrochemical Cells: In Situ Formation of a Light-Emitting p—n Junction. J Am Chem Soc. 1996;118(16):3922-3929.
Peng, Kang-Yung, et al., "Efficient Light Harvesting by Sequential Energy Transfer across Aggregates in Polymers of Finite Conjugational Segments with Short Aliphatic Linkages," J. Am. Chem. Soc., 2001, vol. 123, pp. 11388-11397.
Perr et al., Solid phase microextraction ion mobility spectrometer interface for explosive and taggant detection. J Sep Sci. Feb. 2005;28(2):177-83.
Pingarron et al., Carbon fibre microelectrodes modified with rhodium for the electrocatalytic determination of hydrazine. Anal Chim Acta. 2001;439:281-90.
Pinnaduwage, et al., "Detection of 2,4-dinitrotoluene using microcantilever sensors," Sensors and Actuators B, 2004, 99, 223-229.
Pisarevskii et al., Fluoresence spectrum and quantum yield of DNA in solution. Zhurnal Prikladnoi Spektroskipii. 1966;5:621-24.
Place, Ileane, et al., "Stabilization of the Aggregation of Cyanine Dyes at the Molecular and Nanoscopic Level," Langmuir, Jul. 28, 2000, vol. 16, No. 23, pp. 9042-9048.
Pschirer, Neil G., et al., "Poly(fluorenyleneethynylene)s by Alkyne Metathesis: Optical Properties and Aggregation Behavior," Macromolecules, May 9, 2000, vol. 33, No. 11, pp. 3961-3963.

Ratcliffe, Polypyrrole-based sensor for hydrazine and ammonia. Anal Chim Acta. 1990;239:257-62.
Reddinger et al., "Electroactive π-Conjugated Polymers Based on Transition Metal-Containing Thiophenes Capable of Sensing Ionic and Neutral Species," ACS Polym. Prepr., 1997, 321-322.
Reddinger et al., "Electroactive π-Conjugated Polymers Based on Transition Metal-Containing Thiophenes," Synthetic Metals, 1997, 84:225-226.
Reddinger et al., "Tunable Redox and Optical Properties Using Transition Metal-Complexed Polythiophenes," Macromolecules, 1997, 30(3):673-675.
Rendina et al., "Oxidative Addition Reactions of Organplatinum (II) Complexes with Nitrogen-Donor Ligands," J. Chem. Rev. 1997, 1735-54.
Rininsland, F., et al., "Metal ion-mediated polymer superquenching for highly sensitive detection of kinase and phosphatase activities," PNAS, Oct. 26, 2004, 101(43): pp. 15295-15300.
Rininsland, F., et al., "High-throughput kinase assays with protein substrates using fluorescent polymer superquenching," BMC Biotechnology, vol. 5, No. 16 (2005). 6 pages.
Rose et al., "Excited-State Lifetime Modulation in Triphenylene-Based Conjugated Polymers," J. Am. Chem. Soc., 2001, 123:11298-11299.
Rose et al., Sensitivity gains in chemosensing by lasing action in organic polymers. Nature. Apr. 14, 2005;434(7035):876-9.
Sandrini et al., "Photochemistry of the Orthometalated cis-Bis[2-(2-thienyl)pyridine]platinum(II) Complex in Halocarbon Solvents," J. Am. Chem. Soc. 1987, 109, 7720-24.
Schwarz et al., "Spectroscopic Studies of Cyclometalated Platinum(II) Complexes: Optical Absorption and Emission of Single-Crystal cis-Bis(benzo[h]quinolinato)platinum(II)," Inorg. Chem. 1989, 28, 1053-59.
Segawa et al., "Approaches to conducting polymer devices with nano-structure: Electrochemical construction of one-dimensional and two-dimensional prophyrin-oligothiophene co=polymers," Synthetic Metals, 1995, 71:2151-2154.
Shabani et al., Indirect Spectrophotometric Determination of Trace Quantities of Hydrazine. Bull Korean Chem Soc. 2004;25:213-15.
Shamiryan, D. et al., "Low-k dielectric materials," Materials Today, Jan. 2004. 34-39.
Shimidzu et al., "Approaches to conducting polymer devices with nanostructures: photoelectrochemical function of one-dimensional and two-dimensional porphyrin polymers with oligothienyl molecular wire," Journal of Photochemistry and Photobiology A: Chemistry 99, 1995, Article 4168:1-7.
Smet, M. et al., "Synthesis of the Formal Diels-Alder Adducts of N-substituted Dehydromaleimides and Anthracene," Molecules 2000, 5, 179-188.
Snow A.W., et al., "Synthesis and Evaluation of Hexafluorodimethylcarbinol Functionalized Polymers as Microsensor Coatings," Journal of Applied Polymer Science, 1991, vol. 43, pp. 1659-1671.
Swager, Timothy M., "The Molecular Wire Approach to Sensory Signal Amplification," Acc. Chem. Res., 1998, vol. 31, No. 5, pp. 201-207.
Swager, Timothy M., et al., "Fluorescence Studies of Poly(p-phenyleneethynylene)s: The Effect of Anthracene Substitution," J. Phys .Chem., 1995, vol. 99, No. 14, pp. 4886-4893.
Tan, Chunyan, et al., "Photophysics, aggregation and amplified quenching of a water-soluble poly(phenylene ethynylene)," Chem. Commun., 2002, pp. 446-447.
Thomas III, et al., "Molecules and Materials for the Optical Detection of Explosives and Toxic Chemicals," Dissertation, Massachusetts Institute of Technology, Jun. 2006.
Thomas III, et al., "Towards chemosensing phosphorescent conjugated polymers: cyclometalated platinum(II) poly(phenylene)s," J. Mater. Chem. 2005, 2829-2835.
Thomas, III et al. "Designing Amplifying Polymer Sensors for Explosives and Toxic Chemicals," Polymeric Materials: Science and Engineering 2006, 95, 81-82.
Thomas, III et al. "Trace Hydrazine Detection with Fluorescent Conjugated Polymers: A Turn-On Sensory Mechanism," Adv. Materials 2006, 18, 1047-1050.

(56) References Cited

OTHER PUBLICATIONS

Thomas, III et al., "Amplifying fluorescent polymer sensors for the explosives taggant 2,3-dimethyl-2,3-dinitrobutane (DMNB)," Chem. Commun. 2005, 4572-4574.
Thomas, III et al., "Conjugated Polymer Sensors: Design Principles Towards Enhanced Versatility," presented at the Army Science Conference, Dec. 2004.
Thomas, III et al., "Conjugated Polymer Sensors: Detection of DMNB and Hydrazine," presented at the Materials Research Symposium, Boston, MA (Dec. 2005).
Thomas, III et al., "Conjugated Polymer Sensors: Detection of DMNB and Hydrazine," presented to the American Chemical Society at the 230$^{th}$ National Meeting, Washington, D.C. (Aug. 28-Sep. 1, 2005).
Thomas, III et al., "Dark-Field Oxidative Addition-Based Chemosensing: New Bis-cyclometalated Pt(II) Complexes and Phosphorescent Detection of Cyanogen Halides," J. Am. Chem. Soc. 2006, 128, 16641-16648.
Thomas, III et al., "Synthesis and Optical Properties of Simple Amine-Containing Conjugated Polymers," Macromolecules, 2005, 38(7), 2716-2721.
Toal et al., Polymer sensors for nitroaromatic explosives detection. J Mater Chem. 2006;16:2871-83.
Treichel, H. et al., "Integration Challenges for Low Dielectric Constant Materials," Advanced Engineering Materials. 2001;7(3):461-64.
Tsai et al., New Thiophene-Linked Conjugated Poly(azomethine)s: Theoretical Electronic Structure, Synthesis, and Properties. Macromolecules. 2005;38:1958-66.
Van Houten, Kelly A., et al., "Rapid Luminescent Detection of Phosphate Esters in Solution and the Gas Phase Using (dppe)Pt{S2C2(2-pyridyl)(CH2CH2OH)}," J. Am. Chem. Soc., 1998, vol. 120, No. 47, pp. 12359-12360.
Vilas-Boas et al., "New Insights into the Structure and Properties of Electroactive Polymer Films Derived from [Ni(salen)]," Inorganic Chemistry, 1997, 36(22):4919-4929.
Virji et al., Hydrazine Detection by Polyaniline Using Fluorinated Alcohol Additives. Chem Mater. 2005;17(5):1256-1260.
Virji et al., Polyaniline Nanofiber Gas Sensors: Examination of Response Mechanisms. Nano Letters. 2004;4(3):491-496.
Von Zelewsky et al., "Thermal and Photochemical Oxidative Addition of Alkyl Halides to the Cyclometalated Complex cis-Bis[2-(2'-thienyl)pyridine]platinum(II)," Inorg. Chem. 1993, 32, 4585-93.
Walters, Keith A., et al., "Photophysical Consequences of Conformation and Aggregation in Dilute Solutions of π-Conjugated Oligomers," Langmuir, 1999, vol. 15, pp. 5676-5680.
Waluk, "Hydrogen-Bonding-Induced Phenomena in Bifunctional Heteroazaaromatics," Acc. Chem. Res. 2003, 36, 832-838.
Wang et al., Catalytic-adsorptive stripping voltammetric measurements of hydrazines. Talanta. Dec. 1988;35(12):965-8.
Wang et al., Hydrazine Detection Using a Tyrosinase-Based Inhibition Biosensor. Anal Chem. 1995;67:3824-27.
Wang, C., et al., "Biosensors from conjugated polyelectrolyte complexes," PNAS, 2002, 99(1): pp. 49-53.
Wang, D., et al. "Photoluminescence Quenching of Conjugated Macromolecules by Bipyridinium Derivatives in Aqueous Media: Charge Dependence,"Langmuir, 2001, 17(4): 1262-1266.
Wang, J., et al., "Photoluminescence of Water-Soluble Conjugated Polymers: Origin of Enhanced Quenching by Charge Transfer," Macromolecules 2000, 33(14): 5153-5158.
Wang, S., et al., "Fluorescein Provides a Resonance Gate for FRET from Conjugated Polymers to DNA Intercalated Dyes," J. Am. Chem. Soc., vol. 126, pp. 5446-5451 (2004).
Weder, Christoph, et al., "Efficient Solid-State Photoluminescence in New Poly(2,5-dialkoxy-p-phenyleneethynylene)s," Macromolecules, 1996, vol. 29, No. 15, pp. 5157-5165.
Whitten, D., et al., "From Superquenching to Biodetection: Building Sensors Based on Fluorescent Polyelectrolytes" Optical Sensors and Switches, pp. 189-208 (2001).
Willis et al., Fluoresence decay kinetics of tyrosinate and tyrosine hydrogen-bonded complexes. J Physical Chemistry 1991;95:1585-89.
Wolfbeis, "Materials for fluorescence-based optical chemical sensors," J. Mater. Chem., 2005, 15, 2657-2669.
Wosnick et al., "Layer-by-Layer Poly(phenylene ethynylene) Films on Silica Microspheres for Enhanced Sensory Amplification," Macromolecules, 2005, 38(22), 9287-9290.
Wosnick et al., "Synthesis and Application of Poly(phenylene Ethynylene)s for Bioconjugation: A Conjugated Polymer-Based Fluorogenic Probe for Proteases," J. Am. Chem. Soc., 2005, 127(10), 3400-3405.
Wu et al., "Preparation and Encapsulation of Highly Fluorescent Conjugated Polymer Nanoparticles," Langmuir, 2006, 22(7), 2956-2960.
Wu et al., Novel water-soluble fluorescent polymer containing recognition units: Synthesis and interactions with PC12 cell. Euro Polymer J. 2005;41:1985-1992.
Wu, Chi, et al., "Novel Nanoparticles Formed via Self-Assembly of Poly(ethylene glycol-b-sebacic anhydride) and Their Degradation in Water," Macromolecules, Oct. 31, 2000, vol. 33, No. 24, pp. 9040-9043.
Xia, et al., "A high-throughput screening assay for Kinases and Phosphatases via metal ion-mediated fluorescent polymer superquenching," American Laboratory, Oct. 2004, 36(20): pp. 15-19.
Xia, W., et al., "Applications of fluorescent polymer superquenching to high throughput screening assays for protein kinases," A&DDT, Apr. 2004, 2(2): pp. 183-192.
Yamaguchi et al., Light-emitting efficiency tuning of rod-shaped pi conjugated systems by donor and acceptor groups. J Am Chem Soc. Jul. 6, 2005;127(26):9332-3.
Yang et al.,Growth of Ultrathin Covalently Attached Polymer Films: Uniform Thin Films for Chemical Microsensors. Langmuir. 1998;14:1505-07.
Yang, Jye-Shane, et al., "Anomalous crystal packing of iptycene secondary diamides leading to novel chain and channel networks," Tetrahedron Letters, Oct. 7, 2000, vol. 41, Issue 41, pp. 7911-7915.
Yang, Jye-Shane, et al., "Fluorescent Porous Polymer Films as TNT Chemosensors: Electronic and Structural Effects," J. Am. Chem. Soc., 1998, vol. 120, No. 46, pp. 11864-11873.
Yang, Jye-Shane, et al., "Porous Shape Persistent Fluorescent Polymer Films: An Approach to TNT Sensory Materials," J. Am. Chem. Soc., Jun. 3, 1998, vol. 120, No. 21, pp. 5321-5322.
Yu et al., New efficient blue light emitting polymer for light emitting diodes. Chem Commun. 1999:1837-38.
Yuan et al., +Fiber optic chemical sensors using a modified conducting polymer cladding . SPIE. 2001;4205:170-79.
Zahn et al., "Three-Dimensional Electronic Delocalization in Chiral Conjugated Polymers," Angew. Chem. Int. Ed. Engl., 2002, 41(22):4226-4230.
Zhang et al., Fluorescent Detection of Chemical Warfare Agents: Functional Group Specific Ratiometric Chemosensors. Supporting Information. Downloaded from http://pubs.acs.org/subscribe/journals/jacsat/suppinfo/ja029265z/ja029265zsi20030125_030500. pdf. Date unknown.
Zhang et al., Fluorescent detection of chemical warfare agents: functional group specific ratiometric chemosensors. J Am Chem Soc. Mar. 26, 2003;125(12):3420-1.
Zhang, Guangzhao, et al., "Formation of Novel Polymeric Nanoparticles," Accounts of Chemical Research, Jan. 6, 2001, vol. 34, No. 3, pp. 249-256.
Zhao et al., "Sensory Responses in Solution vs Solid State: A Fluorescence Quenching Study of Poly(iptycenebutadiynylene)s," Macromolecules, 2005, 38(22), 9377-9384.
Zheng et al., Biotinylated poly(p-phenylene ethynylene): unexpected energy transfer results in the detection of biological analytes. Chem Commun (Camb). Dec. 21, 2004;(24):2798-9. Epub Nov. 4, 2004.
Zheng, J. et al., Supporting Information for "Energy Transfer from Biotinylated Poly)p-phenylene ethynylene): New Insights for Amplified Fluorescence-Based Biosensors" [Chem. Commun., 2004, 2798-2799].

(56) References Cited

OTHER PUBLICATIONS

Zhou et al., Novel Polyphenylenes Containing Phenol-Substituted Oxadiazole Moieties as Fluorescent Chemosensors for Fluoride Ion. Macromolecules. 2005;38:2148-53.
Zhou, Qin, et al. "Fluorescent Chemosensors Based on Energy Migration in Conjugated Polymers: The Molecular Wire Approach to Increased Sensitivity," J. Am. Chem. Soc., 1995, vol. 117, No. 50, pp. 12593-12602.
Zhou, Qin, et al., "Methodology for Enhancing the Sensitivity of Fluorescent Chemosensors: Energy Migration in Conjugated Polymers," J. Am. Chem. Soc., 1995, vol. 117, No. 26 pp. 7017-7018.
Zhu et al., "Conducting Polymetallorotaxanes: A Supramolecular Approach to Transition Metal Ion Sensors," Journal of the American Chemical Society, 1996, 118(36):8713-8714.
Zhu et al., "Design of Conducting Redox Polymers: A Polythiophene-Ru(bipy)3n Hybrid Material," Adv. Mater., 1996, 8(6):497-500.
Zotti et al., "Conductivity in Redox Modified Conducting Polymers. 2. Enhanced Redox Conductivity in Ferrocene-Substituted Polypyrroles and Polythiophenes," Chem. Mater., 1995 7(12):2309-2315.
European Search Report for EP 02024311.9 mailed Jan. 3, 2003.
International Search Report and Written Opinion mailed Feb. 23, 2006, PCT/US2005/033261.
International Preliminary Report on Patentability for PCT/US2005/033261 mailed Mar. 29, 2007.
Invitation to Pay Additional Fees for PCT/US2006/045390 mailed Jun. 12, 2007.
International Search Report and Written Opinion for PCT/US2006/045390 mailed Sep. 24, 2007.
International Preliminary Report on Patentability for PCT/US2006/045390 mailed Jun. 5, 2008.
Invitation to Pay Additional Fee for PCT/US2007/017380 mailed Jan. 4, 2008.
International Search Report and Written Opinion mailed Apr. 8, 2008 in PCT/US2007/017380.
International Preliminary Report on Patentability mailed Nov. 10, 2008 in PCT/US2007/017380.
International Search Report and Written Opinion mailed Dec. 14, 2007 in PCT/US2007/020961.
International Preliminary Report on Patentability dated Mar. 31, 2009, mailed Apr. 9, 2009, in PCT/US2007/020961.
Invitation to Pay Additional Fee for PCT/US2007/020992 mailed Feb. 8, 2008.
International Search Report and Written Opinion for PCT/US2007/020992 mailed Apr. 4, 2008.
International Preliminary Report on Patentability for PCT/US2007/020992 mailed Apr. 9, 2009.
International Search Report and Written Opinion mailed Oct. 27, 2008 in PCT/US2007/022670.
International Preliminary Report on Patentability dated Apr. 28, 2009, mailed May 7, 2009, in PCT/US2007/022670.
Invitation to Pay Additional Fee for PCT/US2007/021370 mailed Feb. 22, 2008.
International Search Report and Written Opinion mailed Jun. 13, 2008 in PCT/US2007/021370.
International Preliminary Report on Patentability for PCT/US2007/021370 mailed Apr. 16, 2009.

SENSOR OF SPECIES INCLUDING TOXINS AND CHEMICAL WARFARE AGENTS

RELATED APPLICATIONS

This application is a continuation of U.S. patent application Ser. No. 11/588,881, filed Oct. 27, 2006, entitled "Sensor of Specifies Including Toxins and Chemical Warfare Agents," which is incorporated herein by reference in its entirety for all purposes.

STATEMENT REGARDING FEDERALLY SPONSORED RESEARCH OR DEVELOPMENT

This invention was made with government support under grant number DMR0314421 awarded by the National Science Foundation. The government has certain rights in this invention.

FIELD OF THE INVENTION

The present invention relates to luminescent materials, including metal complexes, and related methods.

BACKGROUND OF THE INVENTION

Phosphorescent, heavy metal complexes have been shown to form triplet state excitons upon electron-hole recombination. The phosphors may harness the energy of such triplet excitons and convert them into useful light output, which can often be more efficient then fluorescence-based output. As a result, many heavy metal complexes have been used in phosphorescence-based organic light emitting devices (OLEDs). Among the most popular classes of heavy metal complexes used in phosphorescent OLEDs are those that are cyclometallated with bidentate ligands, such as 2-phenylpyridine. In the absence of oxygen, these complexes are often highly emissive in solution due to the large ligand field induced by the metal-carbon bond, which raises the energy of the non-emissive d-d metal centered transitions above the triplet energy of the cyclometalated ligand. The presence of the heavy metal can serve to increase the intersystem crossing rate through spin-orbit coupling and reduce the forbidden character of emission from the triplet state of the ligand. Most often, these complexes display ligand-centered based phosphorescence ($^3$LC). The structures of the ligands can be varied to enhance emission intensity and color purity.

SUMMARY OF THE INVENTION

The present invention provides methods for determination of an analyte comprising exposing a metal complex having a luminescence emission to a sample suspected of containing an analyte, wherein the analyte, if present, interacts with the metal complex via an oxidative addition reaction to produce a change in the luminescence emission of the metal complex; and determining the change in luminescence emission of the metal complex, thereby determining the analyte.

The present invention also provides methods for determination of an analyte comprising exposing a metal complex having a luminescence emission to a sample suspected of containing an analyte, wherein the analyte, if present, interacts with the metal complex to produce a change in the luminescence emission of the metal complex, wherein the metal complex has the structure, $L^1$-M-$L^2$, wherein M is a metal, and $L^1$ and $L^2$ can be the same or different and, when bound to the metal, $L^1$ and $L^2$ are bidentate cyclometallated ligands; and determining the change in luminescence emission of the complex, thereby determining the analyte.

The present invention also relates to sensors comprising a metal complex having the structure, $L^1$-M-$L^2$, wherein M is a metal, and $L^1$ and $L^2$ can be the same or different and, when bound to the metal, $L^1$ and $L^2$ are bidentate cyclometallated ligands, a source of energy applicable to the metal complex to cause an emission of radiation, and an emission detector positioned to detect the emission.

The present invention also relates to compositions of matter comprising a compound having the following structure, $L^1$-M-$L^2$, wherein M is a metal, and $L^1$ and $L^2$ can be the same or different and each is a bidentate ligand having the structure,

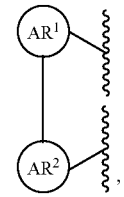

wherein $Ar^1$ and $Ar^2$ can be the same or different and are aryl or heteroaryl, optionally substituted, or $Ar^1$ and $Ar^2$ together form a fused polycyclic aromatic group, optionally substituted, provided that when $L^1$ and $L^2$ are the same, $L^1$ and $L^2$ are not phenylthiophene, thienylpyridine, benzoquinoline, 1-phenylpyrazole, or 2-thienylpyrazole.

The present invention also provides methods of synthesizing a bis-cyclometallated metal complex comprising halogenating at least one bidentate ligand having the follow structure,

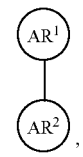

to form a halogenated bidentate ligand, wherein $Ar^1$ and $Ar^2$ can be the same or different and are aryl or heteroaryl, optionally substituted, or $Ar^1$ and $Ar^2$ together form a fused polycyclic aromatic group, optionally substituted; and forming a metal complex between the halogenated bidentate ligand and a metal.

The present invention also provides methods for determination of an analyte comprising providing a luminescent material having a first emission at a wavelength; exposing the luminescent material to a sample suspected of containing an analyte, wherein the analyte, if present, interacts with the luminescent material to produce a second emission at said wavelength, wherein the luminescence intensity of the second emission is at least 10 times greater than the luminescence intensity of the first emission; and determining the second emission, thereby determining the analyte.

BRIEF DESCRIPTION OF THE DRAWINGS

FIG. 18A shows a photograph of a PMMA film containing complex 3a.

FIG. 18B shows a photograph of a PMMA film containing complex 3a that has been exposed to saturated BrCN vapor for 15 seconds.

FIG. 18C shows a photograph of a PMMA film containing complex 4a.

FIG. 18D shows a photograph of a PMMA film containing complex 4a that has been exposed to saturated BrCN vapor for 15 seconds.

DETAILED DESCRIPTION

The present invention generally relates to emissive materials, devices, and related methods, such as synthetic methods and methods for determination of analytes.

In some cases, the present invention provides sensors and methods for the determination of analytes, wherein the analytes may be determined by monitoring, for example, a change in an optical signal of an emissive material upon exposure to an analyte. The analyte and the emissive material may interact via a chemical reaction, or other chemical, biochemical or biological interaction (e.g., recognition), to form a new emissive species. In some cases, the present invention may be useful in the detection of a wide variety of analytes, such as toxins, chemical warfare agents, and explosives. The present invention also provides emissive compounds including metal complexes that are capable of interacting with an analyte to produce a change in the emission of the compound. Some advantages of the present invention include the determination of analytes with high specificity and sensitivity and the ability to fabricate simplified and highly portable devices.

Figure 1:
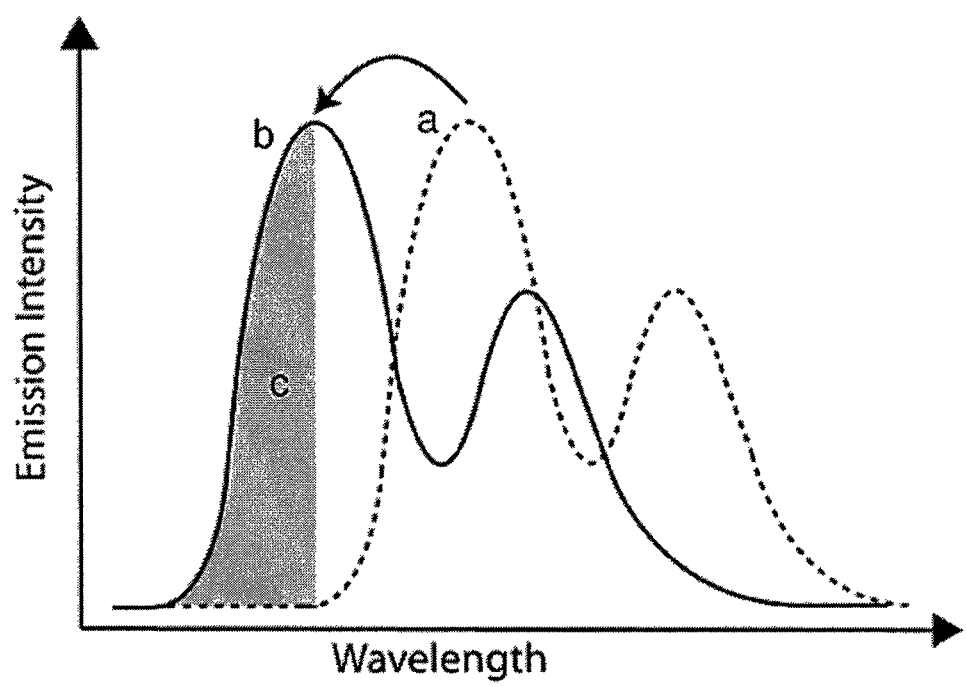
FIG. 1 shows a schematic illustration of a blue-shifting transduction event giving a significant dark-field turn-on signal.

Materials, devices, and methods of the invention may be particularly advantageous in that, in the presence of an analyte, a new signal (e.g., emission) may be generated and/or identified with little or substantially no background noise. For example, in the presence of an analyte, an emissive material may generate a new luminescence emission signal at a wavelength having substantially no signal in the absence of the analyte. In the illustrative embodiment shown in FIG. 1, a material may have an emission signal A in the absence of analyte. In the presence of analyte, emission signal B may be generated by the material, wherein at least a portion of emission signal B does not overlap with emission signal A (e.g., area C). Thus, emission signal A may be more readily distinguished from emission signal B via determination of the signal at area C. The ability to determine a signal with essentially no background noise may allow for more reliable determination of the analyte and may be advantageous in the determination of small quantities of analyte (e.g., parts-per-million or "trace" amounts).

In some cases, in the presence of an analyte, the present invention may advantageously comprise a blue-shifted change in the wavelength of a luminescence emission. As used herein, a "blue-shifted change" or "blue-shift" occurs when the wavelength of an emission shifts to a relatively shorter wavelength of emission, and a "red-shifted change" or "red-shift" occurs when the wavelength of an emission shifts to a relatively longer wavelength of emission. For example, upon exposure to an analyte, a luminescence emission may undergo a blue-shift, e.g., may shift to a shorter wavelength. This may be advantageous over emission-based detection schemes involving a red-shifting of the emission for signal transduction, often by the Förster energy transfer mechanism, since the lower energy vibronic bands of the donor chromophores may often overlap with the acceptor emission, limiting the maximum observable signal-to-noise and decreasing the sensitivity of the measurement. In contrast, a blue-shifted signal transduction event, illustrated schematically in FIG. 1, wherein emission signal A shifts to emission signal B, can allow for monitoring of a large portion (e.g., area C) of the desired signal with substantially no background emission.

In some cases, methods of the invention may comprise exposure of a metal complex having a luminescence emission (e.g., a phosphorescence emission) to a sample suspected of containing an analyte, and, if present, the analyte interacts with the metal complex to cause a change in the emission of the metal complex. Determination of the change in the emission may then determine the analyte. In some cases, the change comprises a decrease or increase in luminescence intensity, and/or a change in the wavelength of the luminescence emission. such as a blue-shifted change. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction. In some embodiments, the interaction between the metal complex and the analyte may comprise a chemical reaction, which may produce a species having an emission (e.g., luminescence emission) that is different from the metal complex. For example, in the absence of analyte, the metal complex may have a first emission, and, upon exposure to the analyte, the analyte interacts with the metal complex to produce a second emission. In some cases, the wavelength of the first emission is separated from the wavelength of the second emission by at least 30 nm, or, in some embodiments, at least 50 nm, at least 100 nm, at least 150 nm, or greater.

As used herein, the term "metal complex" refers to a species formed by the association between a metal atom and at least one chemical moiety coordinated to the metal atom. The association may comprise formation of a covalent bond, and can also comprise the formation of other types of bonds, including ionic bonds, hydrogen bonds (e.g., between hydroxyl, amine, carboxyl, thiol and/or similar functional groups, for example), dative bonds (e.g. complexation or chelation between metal ions and monodentate or multidentate ligands), or the like, and/or other types of interactions between chemical moieties wherein electrons are shared. In some embodiments, the metal complex comprises a metal atom coordinated by at least two bidentate ligands.

Figure 2:
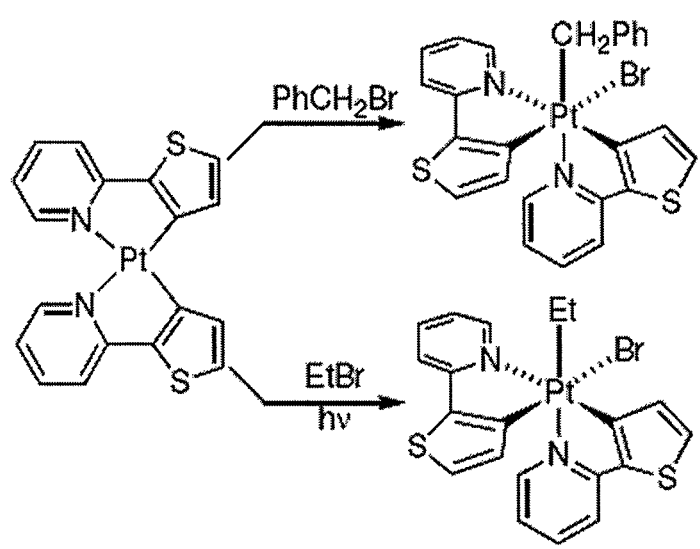
FIG. 2 shows examples of oxidative addition of bis-cyclometallated metal complexes to phenyl bromide and ethyl bromide.

In some embodiments, the interaction between the metal complex and the analyte comprises an oxidative addition reaction. As used herein, the term "oxidative addition" is given its ordinary meaning in the art and refers to the addition of a species to a metal complex, wherein the metal center is oxidized by two electrons (e.g., the metal goes from an "x" oxidation state to an "x+2" oxidation state). For example, Scheme 1 shows the oxidative addition of a species A-B to metal complex $M^{(x)}L_n$ to form a product, $A-M^{(x+2)}L_n$-B. In some embodiments, the metal complex and the analyte may interact via an oxidative addition reaction such that at least one bond is formed therebetween. The metal complexes may undergo oxidative addition with electrophilic species, such as alkyl halides or cyanogen halides, via thermal activation, photochemical activation, or the like. As used herein, an "electrophilic species" refers to a chemical moiety which can accept a pair of electrons from a nucleophile or other species capable of donating a pair of electrons. In some cases, the metal complexes may undergo oxidative addition with a species under ambient conditions. In some cases, the oxidative addition reaction may proceed via a radical mechanism. In some cases, the oxidative addition reaction may proceed via an $S_N2$-type mechanism. FIG. 2 shows an illustrative embodiment wherein a Pt(II) complex comprising two bis-cyclometallated thienylpyridine ligands undergoes oxidative addition with a species, such as benzyl bromide or ethyl bromide. The oxidative addition of A-B to a metal, M, may depend on the relative strengths of the A-B, M-A and M-B bonds. For example, oxidative addition of an alkyl halide may occur more readily than oxidative addition of an alkyl halide.

Scheme 1

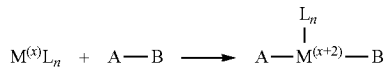

The oxidative addition reaction may produce a change in certain properties of the metal complex, such as geometric configuration, optical properties, and the like. In some cases, the oxidative addition of an analyte to a metal complex may produce a change in the optical properties (e.g., phosphorescence) of the metal complex. In some cases, the optical properties of the material exposed to the analyte may be distinct from those of the material in the absence of the analyte. As an illustrative embodiment, metal(II) complexes having two bis-cyclometallated ligands can be highly reactive via oxidative addition to give the corresponding metal (IV) complexes. In the absence of analyte, the metal(II) complex may have a luminescence emission, wherein, upon oxidative addition of an analyte to produce a metal(IV) complex, the metal(IV) metal complex may have a luminescence emission that is blue-shifted relative to the metal (II) complex. For example, a Pt(II) complex may undergo oxidative addition with an electrophilic species to form a Pt(IV) complexes, wherein the Pt(IV) complex has an emission that is blue-shifted relative to the emission of the Pt(II) complex. Without wishing to be bound by theory, the shift in emission may be attributed to the fact the contribution from a metal-to-ligand charge transfer (MLCT) state in the Pt(II) complexes may be larger than with the Pt(IV) complexes, which may have largely ligand-centered emission.

In some cases, the oxidative addition reaction may also produce a change in the geometric configuration of the metal complex. For example, in the absence of analyte, the metal complex may have a substantially square planar geometry. Upon exposure of the metal complex to an analyte, the analyte may interact with the metal complex to produce a change in the substantially square planar geometry of the metal complex. In some cases, a metal complex having an octahedral geometry may be formed. The conversion of a square planar complex to an octahedral complex is described herein by way of example only, and it should be understood that, in some cases, other geometrical changes occurring upon oxidative addition of a species to a metal complex may be encompassed within the scope of the invention.

The present invention also provides methods for determination of an analyte, wherein, in the presence of analyte, a new emission signal is generated at a wavelength having substantially no emission signal in the absence of the analyte. The method may comprise providing a luminescent material having a first emission at a wavelength, wherein the first emission may have little or substantially no luminescence intensity at said wavelength. Upon exposure of the luminescent material to a sample suspected of containing an analyte, the analyte, if present, may interact with the luminescent material to produce a second emission at said wavelength, wherein the luminescence intensity of the second emission is larger than the luminescence intensity of the first emission. Determination of the second emission may thereby determine the analyte. In the absence of analyte, the first emission may have substantially no luminescence intensity at said wavelength. In some cases, the luminescence intensity of the second emission is at least 10 times greater than the luminescence intensity of the first emission. In some embodiments, the luminescence intensity of the second emission is at least $10^2$, $10^3$, $10^4$, $10^5$, $10^6$, $10^7$, $10^8$, $10^9$, or $10^{10}$ times greater than the luminescence intensity of the first emission.

In some cases, methods of the invention comprise determining a change in the wavelength of an emission signal. For example, the interaction between the analyte and the metal complex may cause a shift in the wavelength of the luminescence intensity of the metal complex, as described herein. In some cases, the change comprises a blue-shifted change in the wavelength of the luminescence emission. The wavelength of the emission of the luminescent material in the presence of analyte may be separated from the wavelength of the emission of the luminescent material in the absence of analyte by at least 30 nm, at least 50 nm, at least 100 nm, at least 150 nm, or greater. The wavelength of an emission signal refers to the wavelength at which the peak maximum of the emission signal occurs in an emission spectrum. The emission signal may be a particular peak having the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum. In some cases, upon exposure to the analyte, the second emission signal may be generated at a wavelength having substantially no emission signal in the absence of analyte (e.g., "dark-field"). In some cases, the second emission signal may be red-shifted, i.e., may occur at a longer wavelength, relative to the first emission. In some cases, the second emission signal may be blue-shifted, i.e., may occur at a shorter wavelength, relative to the first emission.

In some embodiments, methods of the invention may also comprise determining a change in the luminescence intensity of an emission signal. The change in luminescence intensity may occur for an emission signal with substantially no shift in the wavelength of the luminescence (e.g., emission), wherein the intensity of the emission signal changes but the wavelength remains essentially unchanged. In other embodiments, the change in luminescence intensity may occur for an emission signal in combination with a shift in the wavelength of the luminescence (e.g., emission). For example, an emission signal may simultaneously undergo a shift in wavelength in addition to an increase or decrease in luminescence intensity. In another embodiment, the change may comprise two emission signals occurring at two different wavelengths, wherein each of the two emission signals undergoes a change in luminescence intensity. In some cases, the two emission signals may undergo changes in luminescence intensity independent of one another. In some cases, the two emission signals may undergo changes in luminescence intensity, wherein the two emission signals are associated with one another, for example, via an energy transfer mechanism, as described more fully below.

Methods of the present invention may also comprise determining a change in luminescence intensity in combination with a change in the luminescence wavelength, upon exposure of the metal complex to an analyte. For example, the relative luminescence intensities of a first emission signal and a second emission signal associated with the first emission signal may be modulated using the methods described herein. In some cases, the first emission signal and the second emission signal may be associated with (e.g., interact with) one another via an energy transfer mechanism, such as fluorescence resonance energy transfer, for example. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species.

In one embodiment, a first luminescent species may act as FRET donor and a second luminescent species may act as a FRET acceptor, wherein the first portion and the second portion each have different emission wavelengths. The first luminescent species may be associated with a quenching molecule and exist in a "quenched" state, wherein, upon exposure of the first portion to electromagnetic radiation, the quenching molecule absorbs the excitation energy and substantially no emission is observed. Upon exposure to an analyte, the analyte may interact with the first luminescent species and/or quenching molecule to "un-quench" the first luminescent species. As a result, exposure of the first luminescent species to electromagnetic radiation produces an excited-state, wherein the first luminescent species may transfer excitation energy to the second luminescent species, and emission signal from the second luminescent species is observed.

In some cases, the emission may also be visible by sight, e.g., the metal complex may emit visible light. This may allow for the determination of analytes via a colorimetric change. For example, the metal complex, in the absence of analyte, may have a first color, and, upon exposure to an analyte and irradiation by a source of energy, the metal complex may have a second color, wherein the change in color may determine the analyte.

Some embodiments of the invention provide compositions of matter comprising a metal complex having the following structure,

wherein M is a metal, and $L^1$ and $L^2$ can be the same or different and each is a bidentate ligand (e.g., bidentate cyclometallated ligand) having the structure,

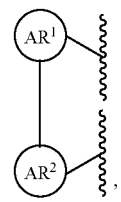

wherein $Ar^1$ and $Ar^2$ can be the same or different and are aryl or heteroaryl, optionally substituted, or $Ar^1$ and $Ar^2$ together form a fused polycyclic aromatic group, optionally substituted, provided that when $L^1$ and $L^2$ are the same, $L^1$ and $L^2$ are not phenylthiophene, thienylpyridine, benzoquinoline, 1-phenylpyrazole, or 2-thienylpyrazole. In some embodiments, $L^1$ and $L^2$ are independently phenylthiophene, thienylpyridine, thianapthylpyridine, or substituted derivatives thereof. In some embodiments, M is platinum, iridium, or palladium. In some embodiments, M is platinum. In some embodiments, M is a metal, and $L^1$ and $L^2$ can be the same or different and, when bound to the metal, $L^1$ and $L^2$ are bidentate cyclometallated ligands. Such metal complexes may be used in sensors and methods as described herein.

In one embodiment, the compound has the structure,

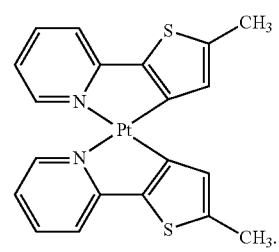

In another embodiment, the compound has the structure,

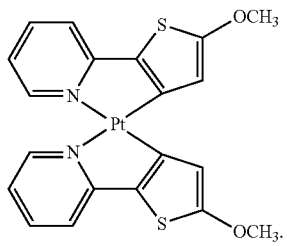

In another embodiment, the compound has the structure,

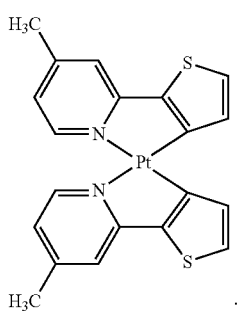

In another embodiment, the compound has the structure,

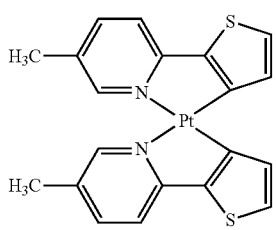

In another embodiment, the compound has the structure,

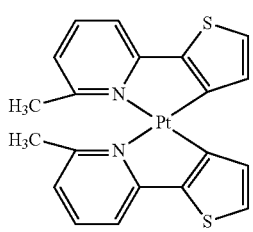

In another embodiment, the compound has the structure,

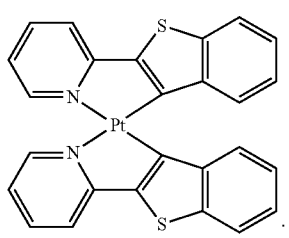

In another embodiment, the compound has the structure,

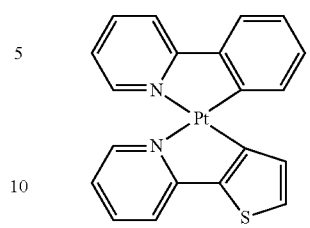

The present invention also provides methods for synthesizing a bis-cyclometallated metal complexes, comprising halogenating at least one bidentate ligand having the follow structure,

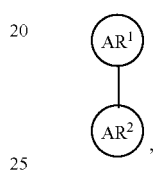

to form a halogenated bidentate ligand, wherein $Ar^1$ and $Ar^2$ can be the same or different and are aryl or heteroaryl, optionally substituted, or $Ar^1$ and $Ar^2$ together form a fused polycyclic aromatic group, optionally substituted. The metal complex may then be formed between the halogenated bidentate ligand and a metal. In some embodiments, the method further comprises lithiating the halogenated bidentate ligand, prior to forming the metal complex. The introduction of a halide to the bidentate ligand, optionally followed by lithiation of the halogenated bidentate ligand, may facilitate and/or direct coordination of the ligand to the metal center to product the desired product. For example, a lithium reagent may be more reactive towards a carbon-halogen bond relative to a carbon-hydrogen bond, and, thus, halogenation of a bidentate ligand at a particular desired position, followed by selective lithiation of the carbon-halogen bond, may allow for the metal to coordinate at the particular position. As used herein, the term "halogenating" is given its ordinary meaning in the art and refers to substituting an atom, such as hydrogen, of a molecule with a halogen atom. For example, a hydrogen of an aromatic group may be substituted with a halogen. In some cases, the halogenating step comprises exposure to bromine ($Br_2$), N-bromosuccinimide (NBS), or the like, either alone or in combination with other reagents including $Pd(OAc)_2$ and $Hg(OAc)_2$. For example, the halogenating step may comprise exposure to NBS and $Pd(OAc)_2$, or, $Br_2$ and $Hg(OAc)_2$. Those of ordinary skill in the art would be able to select the appropriate reagents to achieve a particular halogenated product.

In some embodiments, the halogenated bidentate ligand may be combined with a metal or metal-containing compound to form the metal complex. The metal may be, for example, platinum, iridium, or palladium. In one embodiment, the metal is platinum. In some cases, each bidentate ligand can be the same or different and can be phenylthiophene, thienylpyridine, thianapthylpyridine, benzoquinoline, or a substituted derivative thereof.

Figure 3:
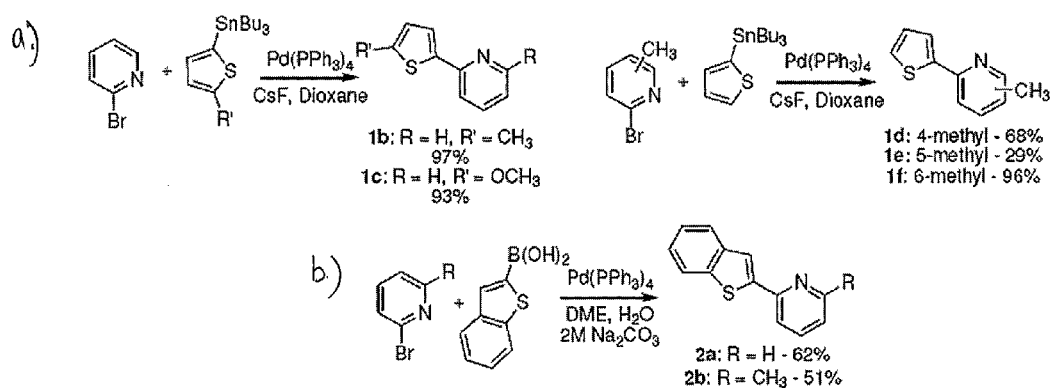
FIGS. 3A-B shows the syntheses of thienylpyridine ligands, according to some embodiments of the invention.

The illustrative embodiments shown in FIGS. 3A-B show the syntheses of thienylpyridine ligands, according to some embodiments of the invention. Bi- or tri-cyclic ligands may be readily synthesized by, for example, palladium-catalyzed cross-coupling methods. For example, a Suzuki coupling between thiophene 2-boronic acid and 2-bromopyridine may produce thienylpyridine (ligand 1a), while Stille couplings with the appropriately substituted reactants, either commercially available or readily prepared, may produce ligands 1b-1f (FIG. 3A). Benzothiophene-based ligands 2a and 2b may be prepared from commercially available thianapthene boronic acid and 2-bromopyridine by Suzuki coupling (FIG. 3B).

Figure 4:
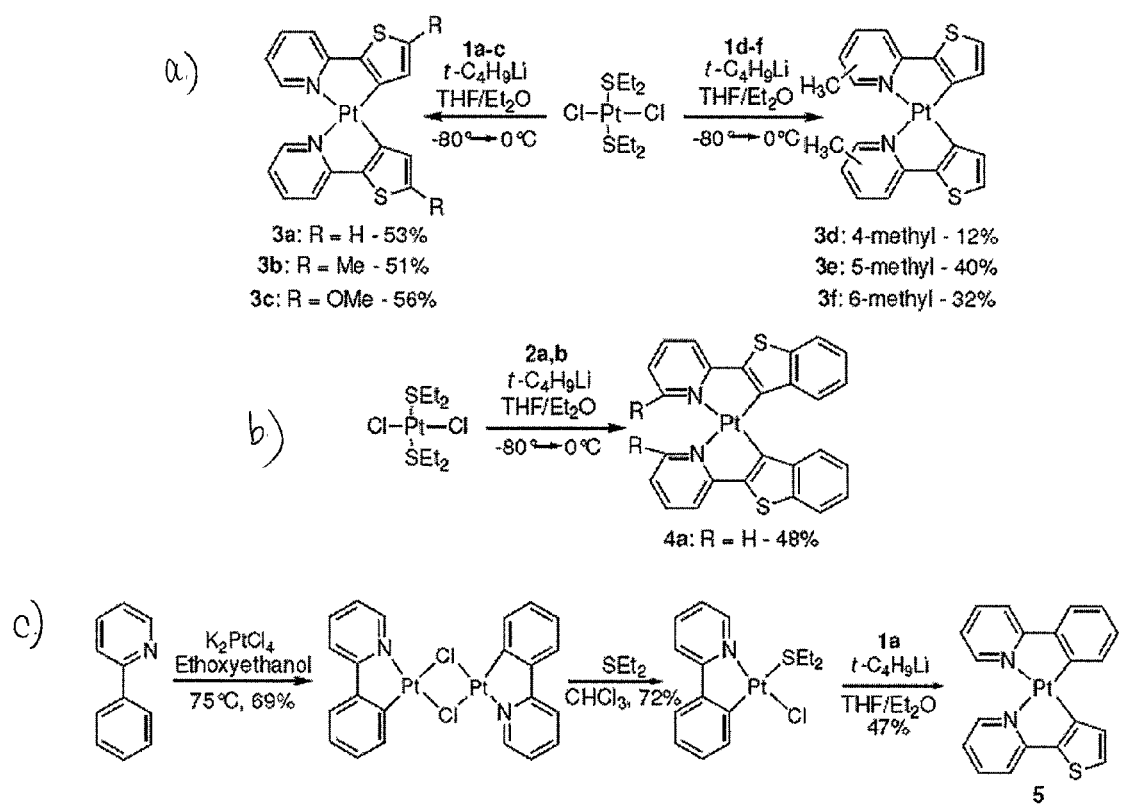
FIGS. 4A-C show the syntheses of bis-cyclometalated Pt(II) complexes, according to some embodiments of the invention.

FIGS. 4A-C show the syntheses of bis-cyclometalated Pt(II) complexes. In some embodiments, homoleptic complexes may be synthesized by lithiation of the ligand with t-butyllithium in a $THF/Et_2O$ mixture, followed by metallation (FIGS. 4A-B). For example, the lithiated ligand may be metallated with $Cl_2Pt(SEt_2)_2$. In some embodiments, heteroleptic complexes may be prepared by cracking a halide-bridged ligand dimer. As shown in FIG. 4C, a chloro-bridged ppy-ligated dimer intermediate was cracked with diethyl sulfide, followed by reaction with the lithiated thpy ligand. The metal complexes may be purified via chromatography under ambient conditions on silica gel and isolated as single stereoisomers.

The present invention also relates to sensors for the determination of analytes, wherein the sensors comprise metal complexes, as described herein, which may be capable of undergoing an oxidative addition reaction with an analyte. The metal complex may be in solution (e.g., benzene solution, toluene solution, tetrahydrofuran solution, or the like) or in solid form. For example, the sensor may further comprise a solid support material, wherein the metal complex is dispersed within the support material. In some cases, the support material may be a polymer, such as poly(methyl methacrylate). The metal complex may be bonded to the support material via covalent bonds or non-covalent bonds. In some cases, the metal complex may be covalently bonded to the support material, such as a polymer. In some cases, the metal complex may be covalently bonded to a polymer backbone via a pendant side group. In some cases, the metal complex may be positioned within a polymer backbone. In some embodiments, the metal complex may be dispersed within the support material (e.g., non-covalently dispersed). In some cases, the solution or support material may comprise at least 1 wt % of metal complex, or, in some embodiments, at least 5 wt % of metal complex, at least 10 wt % of metal complex, at least 25 wt % of metal complex. In one embodiments, the solution or support material comprises 10 wt % of metal complex.

The sensor may further comprise at least one source of energy applicable to the metal complex. In some cases, the source of energy, when applied to the metal complex, may cause an emission of radiation from the metal complex. The source of energy may be an electric, magnetic, optical, acoustic, electromagnetic, or mechanical field. In some embodiments, the source of energy is electromagnetic radiation. The sensor may further comprise an emission detector positioned to detect the emission. The source of energy can be provided in combination with the metal complex and/or sensor in a variety of ways, such as being integrally and/or functionally connected to the metal complex/sensor (for example, by providing a compartment or other assembly supporting both the metal complex/sensor and the energy source), or in combination such that the metal complex/sensor and energy source can be used together (e.g., packaged together, or otherwise provided together and with the ability to arrange each, with respect to the other, for use as described herein). The emission detector can be provided in combination with the metal complex and/or sensor, in a manner as described above with respect to the energy source. Where the energy source and emission detector are both provided in combination with the metal complex/sensor, they can be provided in essentially identical or similar structural relation to the metal complex/sensor (e.g., both attached to a common housing or framework, to which the metal complex/sensor is also attached), or their relationship to the metal complex/sensor can differ.

In some embodiments, sensors of the invention may comprise an inlet for intake of a sample (e.g., vapor sample, solution sample), a sample cell comprising the metal complex, the sample cell constructed and arranged to receive the sample, and a detection mechanism in optical communication with the sample cell. Systems such as this may be useful in the determination of, for example, electrophilic analytes such as a cyanogen halide. As used herein, a sample cell "constructed and arranged" refers to a sample cell provided in a manner to direct the passage of a sample, such as a sample comprising a cyanogen halide, from the inlet into the sample cell, such that the vapor sample contacts the metal complex. "Optical communication" may refer to the ability of the detection mechanism to receive and detect an optical signal (e.g., light emission) from the sample cell.

Methods for synthesizing sensors as described herein may comprise forming a fluid mixture comprising the metal complex and a support material or support material precursor, and solidifying the fluid mixture to produce a solid composition that is emissive upon exposure to a source of energy, such as electromagnetic radiation. In certain cases, forming the fluid mixture may comprise providing the support material or support material precursor as a fluid, and dissolving or suspending the metal complex in the fluid support material precursor. In some embodiments, forming the fluid mixture may comprise providing the support material as a solid, and suspending (i.e., immersing) the support material in the fluid mixture.

In some embodiments, forming the fluid mixture may comprise dissolving or suspending the metal complex and support material or support material precursor in an auxiliary fluid. In some embodiments, the auxiliary fluid is a solvent, such that forming the fluid mixture comprises dissolving the metal complex and support material or support material precursor in the solvent. Optionally, a catalyst, acid, base, buffer, and/or other additives (e.g., plasticizers, etc.) may be added to the fluid mixture. Solidification of the fluid mixture may comprise, in cases where a solvent is employed as an auxiliary fluid, removal of a solvent by, for example, evaporation or filtration. Solidification of the fluid mixture may also comprise, in cases where the support material precursor is provided as a fluid, conversion of the support material precursor to a support material (e.g., a solid support material).

As used herein, an emitted radiation or "emission" may be luminescence emission, in which "luminescence" is defined as an emission of ultraviolet or visible radiation. Specific types of luminescence include fluorescence, phosphorescence, chemiluminescence, electrochemiluminescence, other types of luminescence, and the like. In some cases, the emission may be phosphorescence emission.

As described herein, metal complexes of the invention comprise a metal center. Metals (e.g., metal centers) which are suitable for use in the invention include metals which are capable of coordinating ligands as described herein, as well as those which are capable of undergoing an oxidative addition reaction. For example, metal centers that are not in their highest oxidation state may undergo oxidative addition reactions. In some cases, the oxidative addition reaction may proceed more readily if the starting and final oxidation states of the metal center are relatively stable. The metal center may also be selected such that it forms a metal complex capable of generating an emission, such as a phosphorescence emission, upon exposure to a source of energy. In some cases, the metal center is a transition metal, such as a heavy metal. Transition metals may include transition metals (e.g., Groups 3-12), lathanides, and actinides. In some cases, the metal is a transition metal from Groups 8-12. In some cases, the metal is a transition metal from Groups 8-10. For example, the metal may be iron, ruthenium, osmium, cobalt, rhodium, iridium, nickel, palladium, or platinum. In some embodiments, the metal is palladium, platinum, or iridium. In a particular embodiment, the metal is platinum.

In some embodiments, metal complexes of the invention may comprise a bidentate ligand which, when bound to a metal center, forms a metallacycle structure with the metal center. Such bidentate ligands, when bound to a metal center, may also be referred to as "bidentate cyclometallated ligands." Bidentate ligands suitable for use in the present invention include species which have at least two sites capable of binding to a metal center. For example, the bidentate ligand may comprise at least two heteroatoms that coordinate the metal center, or a heteroatom and an anionic carbon atom that coordinate the metal center. In some embodiments, the bidentate ligand may be chiral and may be provided as a racemic mixture or a purified stereoisomer. Examples of bidentate ligands suitable for use in the invention include, but are not limited to, aryl and heteroaryl groups (e.g., bis-aryl, heteroaryl-substituted aryl), substituted derivatives there of, and the like.

In some embodiments, the metal complex has two bidentate ligands coordinating the metal center to form a substantially square planar metal complex.

The support material may be any material capable of supporting (e.g., containing) the components (e.g., the metal complex) of the systems described herein. For example, the support material may be selected to have a particular surface area wherein the support material may absorb or otherwise contact a sufficient amount of analyte to allow interaction between the analyte and, for example, the metal complex. In some embodiments, the support material has a high surface area. In some cases, the support material has a surface area of at least 50 $mm^2$, at least 100 $mm^2$, at least 200 $mm^2$, at least 300 $mm^2$, at least 400 $mm^2$, or, more preferably, at least 500 $mm^2$.

In some embodiments, the support material may preferably have a low background signal, substantially no background signal, or a background signal which does not substantially interfere with the signal generated by the metal complex, either in the presence or in the absence of analyte. In some cases, the support material may have a preferred pH to prevent undesirable reactions with, for example, an acid. The support material may be soluble, swellable, or otherwise have sufficient permeability in systems of the invention to permit, for example, intercalation of the metal complex and other components of the system within the support material. In one embodiment, the support material may be hydrophobic, such that a hydrophobic solution containing the metal complex may diffuse or permeate the support material. Additionally, the support material may preferably permit efficient contact between the sample (e.g., analyte) to be determined and the metal complex. For example, in one embodiment, a vapor comprising an analyte may permeate the support material to interact with the metal complex via an oxidative addition reaction. The permeability of certain support materials described herein are known in the art, allowing for the selection of a particular support material having a desired diffusion. The choice of support material may also affect the intensity and duration of light emission from the system.

Examples of support materials include polymers, copolymers, gels, and other solid adsorbent materials. In some embodiments, the support material may be a finely divided powder, particles, molded shapes such as films, bottles, spheres, tubes, strips, tapes, and the like. In some embodiments, the system may have a shape or be formed into a shape (for example, by casting, molding, extruding, and the like). In some embodiments, the support material may be a polymer. Examples of polymers suitable for use as a support material include, but are not limited to, poly(methyl methacrylate), polyethylene, polypropylene, poly(vinyl chloride), poly(vinyl benzoate), poly(vinyl acetate), cellulose, corn starch, poly(vinyl pyrrolidinone)s, polyacrylamides, epoxys, silicones, poly(vinyl butyral)s, polyurethanes, nylons, polacetals, polycarbonates, polyesters and polyethers, polybutadiene copolymers, crosslinked polymers, combinations thereof, and the like. In some cases, the polymer is poly(methylmethacrylate), poly(vinylpyrrolidinone), or poly(4-vinylpyridine). In a particular embodiment, the polymer is poly(methyl methacrylate).

The combination of support material and solvent may have a desired diffusion rate, controlling the intensity and duration of light emission. The permeability of a particular polymer is known in the art.

Analytes that may be determined by devices and methods of the invention include those which are capable of undergoing oxidative addition reactions with metal complexes as described herein. For example, the analyte may be an electrophilic species, such as alkyl halides or cyanogen halides. Some examples of analytes include reactive species such as methyl iodine or benzyl bromide, relatively less reactive molecules, such as chloroform, dichloromethane, or ethyl bromide, or the like. In some cases, the analyte is a cyanogen halide, such as cyanogen chloride, cyanogen bromide, cyanogen iodide, and the like. For example, cyanogen halides (e.g., X—CN, wherein X is a halide) may be highly toxic blood agents that affect the human body in a manner similar to that of hydrogen cyanide. Cyanogen chloride, a gas under ambient conditions, is a military chemical weapon.

As used herein, the term "aryl" refers to an aromatic carbocyclic group having a single ring (e.g., phenyl), multiple rings (e.g., biphenyl), or multiple condensed rings in which at least one is aromatic (e.g., naphthalene, anthracene, or phenanthrene, 1,2,3,4-tetrahydronaphthene, etc.). Aryls groups may ring atoms which are carbon atoms.

The term "heteroaryl" refers to aryl groups which comprise at least one heteroatom as a ring atom, with the remainder of the ring atoms being carbon atoms. Suitable heteroatoms include oxygen, sulfur, nitrogen, phosphorus, and the like. Examples of heteroaryl groups include, but are not limited to, furan, thiophene, pyridine, pyrrole, pyrimidine, pyrazine, imidazole, indole, and the like, all optionally substituted.

The term "fused polycyclic aromatic group" refers to structures with two or more rings (e.g., cycloalkyls, cycloalkenyls, cycloalkynyls, aryls and/or heterocyclyls) in which two or more atoms are common to two adjoining rings, e.g., the rings are "fused rings." In some cases, two rings share two common atoms which are adjacent to one another. Rings that are joined through non-adjacent atoms, e.g., three or more atoms are common to both rings, are "bridged" rings. Examples of fused polycyclic aromatic groups include naphthalene, phenanthrene, and the like.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted thiophene" must still comprise the thiophene moiety and can not be modified or replaced to become, e.g., a furan moiety. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower-carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

EXAMPLES

Example 1

The following general experimental methods were used in the syntheses and studies described herein. All synthetic manipulations were performed under an argon atmosphere using standard Schlenk techniques unless otherwise noted. NMR ($^1$H and $^{13}$C) spectra were recorded on either a Varian Mercury 300 MHz or a Varian INOVA 500 MHz spectrometer. NMR chemical shifts are referenced to residual protonated solvent. High-resolution mass spectra (HRMS) were obtained at the MIT Department of Chemistry Instrumentation Facility using a peak-matching protocol to determine the mass and error range of the molecular ion, using either electron impact or electrospray as the ionization technique.

UV/vis spectra were recorded on an Agilent 8453 diode-array spectrophotometer and corrected for background signal with either a solvent-filled cuvette (for solution measurements) or a clean glass cover slip (for thin film measurements). Emission spectra were acquired on a SPEX Fluorolog-τ3 fluorimeter (model FL-321, 450 W Xenon lamp) using either right angle detection (solution measurements) or front face detection (thin film measurements). All room temperature solution samples for emission spectra were degassed by at least three freeze-pump-thaw cycles in an anaerobic cuvette and were repressurized with Ar following each cycle. 77K emission spectra were acquired in frozen 2-methyltetrahydrofuran glass. Quantum yields of phosphorescence were determined by comparison to Ru(bpy)$_3$ in deoxygenated water and are corrected for solvent refractive index and absorption differences at the excitation wavelength.

Phosphorescence lifetimes were determined by time-resolved phosphorescence spectroscopy. The irradiation source was an Oriel nitrogen laser (Model 79111) with a 5 ns pulsewidth operating at approximately 25 Hz. The emitted light was dispersed in an Oriel MS-260i spectrograph with a 300 lines/mm grating. The detector was an Andor Technologies Intensified CCD camera (1024×128 pixels) with an onboard delay generator and a minimum gate width of 5 ns operating in full vertical binning mode and triggered by a TTL prepulse from the nitrogen laser. Data taken of 77K glasses were subjected to no horizontal binning, while solution data was acquired with a horizontal binning of 2 or 3. 10-15 spectra at different delay times after the laser pulse were taken per lifetime measurement, the integrated intensities of which were fit to a single-exponential function. The detector was calibrated with a Hg(Ar)pencil-style calibration lamp.

X-ray crystal structures were determined with a Siemens Platform three-circle diffractometer coupled to a Bruker-AXS Smart Apex CCD detector with graphite-monochromated Mo Kα radiation λ=0.71073 Å), performing φ- and ω-scans. All structures were solved by direct methods using SHELXS [Sheldrick, G. M., Acta Cryst. Sect. A (1990), 46, 467.] and refined against F$^2$ on all data by full-matrix least squares with SHELXL-97 [Sheldrick, G. M. SHELXL 91, Universität Göttingen, Gottingen, Germany, 1997]. All non-hydrogen atoms were refined anisotropically.

Example 2

Ligand 1b was synthesized according to the following procedure. 2-Bromopyridine (1.48 g, 0.89 mL, 9.4 mmol), 2-methyl-5-(tributylstannyl)thiophene (4.0 g, 10.3 mmol), Pd(PPh$_3$)$_4$ (0.54 g, 0.47 mmol) and CsF (3.12 g, 20.6 mmol) were weighed into a Schlenk tube and 60 mL of dioxane was added. The reaction mixture was sparged for 15 minutes with argon. The reaction mixture was heated at 100° C. for 36 hours. The reaction mixture was cooled down and was passed through a silica gel plug to remove the solids. The silica plug was eluted with 250 mL of ethyl acetate. The combined organic fractions were evaporated to yield an oily residue, which was chromatographed on silica gel with dichloromethane/hexane (2:1 v/v) as the eluant to yield 1.59 g (97%) of 1b as a white solid. $^1$H NMR (500 MHz, CDCl$_3$): δ 8.53 (d, 1H), 7.64 (t, 1H), 7.58 (d, 1H), 7.38 (d, 1H), 7.10 (t, 1H), 6.76 (d, 1H), 2.53 (s, 3H). $^{13}$C NMR (125 MHz, CDCl$_3$) δ 153.0, 149.6, 142.7, 137.7, 126.5, 124.8, 122.6, 118.5, 15.9. HRMS calcd. for C$_{10}$H$_{10}$NS (M+H)$^+$, 176.0529; found, 176.0530. mp=77-78° C.

Example 3

Ligand 1c was synthesized according to the procedure described in Example 2. 2-Bromopyridine (1.63 g, 0.98 mL, 10. mmol), 2-methoxy-5-(tributylstannyl)thiophene (6.0 g, 15 mmol), Pd(PPh$_3$)$_4$ (0.60 g, 0.51 mmol), CsF (3.4 g, 23 mmol). Yield was 1.82 g (93%) using dichloromethane/hexane (2:1 v/v) as the eluant. $^1$H NMR (500 MHz, CDCl$_3$)

δ 8.51 (d, 1H), 7.63 (t, 1H), 7.55 (d, 1H), 7.26 (d, 1H), 7.08 (t, 1H), 6.24 (s, 1H), 3.97 (s, 2H). $^{13}$C NMR (125 MHz, CDCl$_3$) δ 168.7, 153.1, 149.5, 136.5, 130.8, 122.9, 121.1, 117.6, 105.2, 60.3. HRMS calc. for C$_{10}$H$_{10}$NOS (M)$^+$, 192.0478; found, 192.0478. mp=45-46° C.

Example 4

Ligand 1d was synthesized according to the procedure described in Example 2. 2-Bromo-4-methylpyridine (1.5 g, 0.97 mL, 8.7 mmol), 2-(tributylstannyl)thiophene (3.9 g, 3.3 mL, 10. mmol), Pd(PPh$_3$)$_4$ (0.50 g, 0.43 mmol), CsF (1.52 g, 10 mmol). Yield was 1.04 g (68%) using dichloromethane-hexane (3:1 v/v) as the eluant. $^1$H NMR (500 MHz, CDCl$_3$) δ 8.43 9d, 1H), 7.57 (d, 1H), 7.48 (s, 1H), 7.11 (d, 1H), 6.97 (d, 1H), 2.38 (s, 3H). $^{13}$C NMR (125 MHz, CDCl$_3$) δ 52.3, 149.4, 147.9, 145.1, 128.1, 127.5, 124.4, 123.2, 119.8, 21.3. HRMS calc. for C$_{10}$H$_9$NS (M)$^+$, 175.0450; found, 175.0445. mp=39-41° C.

Example 5

Ligand 1e was synthesized according to the procedure described in Example 2. 2-Bromo-5-methylpyridine (1.7 g, 10. mmol), 2-(tributylstannyl)thiophene (3.7 g, 10. mmol), Pd(PPh$_3$)$_4$ (0.1 g, 0.2 mmol), CsF (2.9 g, 19 mmol). Yield was 500 mg (29%) using dichloromethane/hexane (2:1 v/v) and after 2 recrystallizations from hexanes at −78° C. $^1$H NMR (300 MHz, CDCl$_3$) δ 8.37 (s, 1H), 7.45 (m, 3H), 7.33 (d, 1H), 7.07 (t, 1H), 2.30 (s, 3H). $^{13}$C NMR (75 MHz, CDCl$_3$) δ 150.0, 149.8, 145.0, 137.3, 131.6, 128.0, 126.9, 123.9, 118.4, 18.3. HRMS calc. for C$_{10}$H$_9$NS (M$^+$), 175.0450; found, 175.0448. mp=61-63° C.

Example 6

Ligand 1f was synthesized according to the procedure described in Example 2. 2-Bromo-6-methylpyridine (1.15 g, 1.0 mL, 6.69 mmol), 2-(tributylstannyl)thiophene (2.5 g, 2.12 mL, 6.69 mmol), Pd(PPh$_3$)$_4$ (0.386 g, 0.33 mmol), CsF (1.52 g, 10 mmol). Yield was 1.04 g (96%) using dichloromethane/hexane (2:1 v/v) as the eluant. $^1$H NMR (300 MHz, CDCl$_3$) δ 7.58 (m, 2H), 7.44 (d, 1H), 7.37 (d, 1H), 7.11 (t, 1H), 6.98 (d, 1H), 2.59 (s, 3H). $^{13}$C NMR (75 MHz, CDCl$_3$) δ 158.4, 151.9, 145.3, 136.8, 128.0, 127.3, 124.4, 121.5, 115.9, 24.6. HRMS calc. for C$_{10}$H$_{10}$NS (M+H)$^+$, 176.0529; found, 176.0530. mp=38-39° C.

Example 7

Ligand 2a was synthesized according to the following procedure. A 50 mL Schlenk tube was charged with 2.14 g (12 mmol) of thianapthene-2-boronic acid, 0.10 g Pd(PPh$_3$)$_4$ (0.1 mmol). Dimethoxyethane (20 mL) and 5 mL 2M aqueous sodium carbonate were added, and the tube was purged with argon gas with 5 evacuate/refill cycles. 2-Bromo-pyridine (1.58 g, 10.0 mmol) of was added as a neat liquid. The tube was sealed and heated at 90° C. with very vigorous stirring for 2 days. Upon cooling to ambient temperature, the organics were extracted into dichloromethane (3×50 mL) from 50 mL water. The combined organics were washed with water (1×50 mL) and brine (1×50 mL), dried over magnesium sulfate, filtered and dried in vacuo. The crude product was pre-adsorbed onto silica gel and chromatographed (silica gel, 2:1 dichloromethane/hexanes) to give 1.15 g (55%) of 2a as a colorless powder. $^1$H NMR (300 MHz, CDCl$_3$) δ 8.65 (m, 1H), 7.8-7.9 (m, 4H), 7.75 (td, 1H), 7.37 (m, 2H), 7.22 (m, 1H). $^{13}$C NMR (125 MHz, CDCl$_3$) δ 152.7, 149.9, 145.0, 140.8, 140.6, 136.8, 125.2, 124.7, 124.3, 122.8, 122.8, 121.3, 119.8. HRMS calc. for C$_{13}$H$_{10}$NS (M+H)$^+$, 212.0529; found, 212.0534. mp=125-126° C.

Example 8

Ligand 2b was synthesized according to the following procedure. A 50 mL Schlenk tube was charged with 2.14 g (12 mmol) of thianapthene-2-boronic acid, 0.10 g Pd(PPh$_3$)$_4$ (0.1 mmol). 20 mL dimethoxyethane and 5 mL 2M aqueous sodium carbonate were added, and the tube was purged with argon gas with 5 evacuate/refill cycles. 2-Bromo-6-methyl-pyridine (1.72 g, 10.0 mmol) was added as a neat liquid. The tube was sealed and heated at 90° C. with very vigorous stirring for 2 days. Upon cooling to ambient temperature, the organics were extracted into dichloromethane (3×50 mL) from 50 mL water. The combined organics were washed with water (1×50 mL) and brine (1×50 mL), dried over magnesium sulfate, filtered and dried in vacuo. The crude product was pre-adsorbed onto silica gel and chromatographed (silica gel, hexanes to 1:1 dichloromethane/hexanes gradient elution) to give 1.15 g (51%) of 2b as a colorless powder. $^1$H NMR (300 MHz, CDCl$_3$) δ 7.8-7.9 (m, 3H), 7.60 (m, 2H), 7.47 (m, 2H), 7.07 (m, 1H), 2.64 (s, 3H). $^{13}$C NMR (75 MHz, CDCl$_3$) δ 140.7, 140.7, 136.9, 125.0, 124.5, 124.2, 122.7, 122.4, 121.0, 116.8, 24.7. HRMS calc. for C$_{14}$H$_{12}$NS (M+H)$^+$, 226.0685; found, 212.0676. mp=116-117° C.

Example 9

Complex 3a was synthesized according to the following procedure. A solution of trans-PtCl$_2$(Et$_2$S)$_2$ (0.5 g, 1.12 mmol) in diethyl ether and THF was added dropwise to a stirred solution of 4-(2-(2-thienyl)pyridinyl)lithium [from 2-thienylpyridine (0.9 g, 5.6 mmol) and 1.6 M t-Buli (6.56 mL, 11.2 mmol) in ether at −78° C.] in ether at −78° C. After the solution was stirred for 30 min at −78° C., the temperature was allowed to rise slowly to 0° C. The reaction mixture was hydrolyzed (H$_2$O) at 0° C. The organic phase was washed with NaCl solution and the aqueous phase extracted with dichloromethane. The combined extracts were dried (MgSO$_4$). The organic layer was evaporated to yield a red oily residue. The residue was chromatographed on silica gel with dichloromethane:hexane (3:2) as the eluant to give 0.30 g (52%) of 3a as a red solid.

Example 10

Complex 3b was synthesized according to the following procedure. Trans-PtCl$_2$(Et$_2$S)$_2$ (0.50 g, 1.1 mmol) in diethyl ether and THF was added dropwise to a stirred solution of lithiated 19b [from 1b (0.91 g, 5.6 mmol) and 1.6 M t-Buli (6.6 ml, 11 mmol) at −78° C.]. Chromatography on silica gel (2:1 dichloromethane/hexanes) gave 0.31 g of 11b (51%). $^1$H NMR (500 MHz, CDCl$_3$): δ 8.57 (d, 2H), 7.70 (t, 2H), 7.33 (m, 4H), 7.05 (t, 2H), 2.63 (s, 6H). $^{13}$C NMR (125 MHz, CDCl$_3$): δ 162.1, 149.2, 147.8, 143.9, 140.3, 138.7, 134.7, 119.0, 117.6, 16.1. HRMS calc. for C$_{20}$H$_{16}$N$_2$PtS$_2$ (M)$^+$, 543.0392; found, 543.0384.

Example 11

Complex 3c was synthesized according to the following procedure. Trans-PtCl$_2$(Et$_2$S)$_2$ (0.50 g, 1.1 mmol) in diethyl ether and THF was added dropwise to a stirred solution of lithiated 1c [from ligand 1c (1.06 g, 5.6 mmol) and 1.6 M t-BuLi (6.58 mL, 11.2 mmol) at −78° C.]. Chromatography on silica gel (2:1 dichloromethane/hexane) gave 0.36 g of 3c (56%). $^1$H NMR (500 MHz, CDCl$_3$): δ 8.49 (d, 2H), 7.67 (t, 2H), 7.20 (d, 2H), 7.00 (t, 2H), 6.77 (s, 2H), 4.01 (s, 6H). $^{13}$C NMR (125 MHz, CDCl$_3$): δ 170.3, 162.8, 149.3, 147.8, 138.7, 118.1, 116.4, 113.2, 60.7. HRMS calc. for C$_{20}$H$_{16}$O$_2$N$_2$PtS$_2$ (M)$^+$, 575.0290; found, 543.0312.

Example 12

Complex 3d was synthesized according to the following procedure. Trans-PtCl$_2$(Et$_2$S)$_2$ (0.22 g, 0.50 mmol) in diethylether and THF was added dropwise to a stirred solution of lithiated 1d [from ligand 1d (0.35 g, 2.0 mmol) and 1.6 M t-BuLi (2.5 mL, 4.0 mmol) at −78° C.]. Chromatography on silica gel (2:1 dichloromethane/hexane) gave 0.03 g of 3d (12%). $^1$H NMR (500 MHz, CDCl$_3$): δ 8.45 (d, 2H), 7.68 (d, 2H), 7.44 (d, 2H), 7.27 (s, 2H), 6.91 (d, 2H), 2.38 (s, 6H). $^{13}$C NMR (125 MHz, CDCl$_3$): δ 161.5, 160.6, 147.3, 147.2, 142.6, 135.7, 127.6, 121.0, 118.7, 21.6. HRMS calc. for C$_{20}$H$_{16}$N$_2$PtS$_2$ (M)$^+$, 543.0392; found, 543.0403.

Example 13

Complex 3e was synthesized according to the following procedure. Trans-PtCl$_2$(Et$_2$S)$_2$ (0.22 g, 0.50 mmol) in diethylether and THF was added dropwise to a stirred solution of lithiated 1e [from ligand 1e (0.35 g, 2.0 mmol) and 1.6 M t-Buli (2.5 mL, 4.0 mmol) at −78° C.]. Chromatography on silica gel (2:1 dichloromethane/hexane) gave 0.11 g of 3e (40%). $^1$H NMR (500 MHz, CDCl$_3$): δ 8.47 (s, 2H), 7.68 (d, 2H), 7.60 (d, 2H), 7.42 (m, 4H), 2.41 (s, 6H). $^{13}$C NMR (125 MHz, CDCl$_3$): δ 159.5, 147.9, 146.0, 139.5, 135.7, 129.5, 127.2, 117.7, 18.6. HRMS calc. for C$_{20}$H$_{16}$N$_2$PtS$_2$ (M)$^+$, 543.0392; found, 543.0397.

Example 14

Complex 3f was synthesized according to the following procedure. Trans-PtCl$_2$(Et$_2$S)$_2$ (0.28 g, 0.64 mmol) in diethylether and THF was added dropwise to a stirred solution of lithiated 1f [from ligand 1f (0.45 g, 2.5 mmol) and 1.6 M t-Buli (3.2 mL, 5.1 mmol) at −78° C.]. Chromatography on silica gel (2:1 dichloromethane/hexane) gave 0.11 g of 3f (32%). $^1$H NMR (500 MHz, CDCl$_3$): δ 7.65 (d, 2H), 7.56 (t, 2H), 7.40 (d, 2H), 7.26 (d, 2H), 6.91 (d, 2H), 2.61 (s, 6H). $^{13}$C NMR (125 MHz, CDCl$_3$): δ 161.2, 160.1, 146.3, 142.9, 138.5, 135.1, 127.5, 119.9, 114.6, 25.5. HRMS calc. for C$_{20}$H$_{16}$N$_2$PtS$_2$ (M)$^+$, 543.0392; found, 543.0400.

Example 15

Complex 4a was synthesized according to the following procedure. A solution of trans-PtCl$_2$(Et$_2$S)$_2$ (0.25 g, 0.55 mmol) in diethylether and THF was added dropwise to a stirred solution of lithiated 2a [from ligand 2a (0.50 g, 2.2 mmol) and 1.7 M n-BuLi (1.7 mL, 2.2 mmol) in THF at −50° C.] in THF at −78° C. After the solution was stirred for 30 min at −78° C., the temperature was allowed to rise slowly to 0° C. The reaction mixture was hydrolyzed (H$_2$O) at 0° C. The organic phase was washed with NaCl solution and the aqueous phase extracted with dichloromethane. The combined extracts were dried (MgSO$_4$). The organic layer was evaporated to yield a red oily residue. The residue was chromatographed on silica gel with 2:1 dichloromethane/hexane as the eluant to give 0.16 g (48%) of 4a. $^1$H NMR (500 MHz, CDCl$_3$): δ 8.77 (d, 2H), 7.94 (td, 2H), 7.85 (d, 2H), 7.65 (m, 4H), 7.27 (td, 2H), 7.23 (td, 2H), 6.92 (td, 2H). $^{13}$C NMR (125 MHz, CDCl$_3$): δ 147.7, 138.7, 131.3, 125.6, 123.3, 122.3, 121.0, 119.6. HRMS calc. for C$_{26}$H$_{16}$N$_2$PtS$_2$ (M)$^+$, 615.0393; found, 615.0420.

Example 16

Complex 5 was synthesized according to the following procedure. K$_2$PtCl$_4$ (1.0 g, 2.4 mmol) and 2-phenylpyridine (0.68 mL, 4.8 mmol) in a 3:1 mixture of 2-ethoxyethanol (45 mL) and water (15 mL) was heated under argon for 16 hours at 80° C. The reaction mixture was cooled down and poured into 200 mL water to yield a yellow precipitate. The precipitate was filtered, extracted with dichloromethane and dried over Na$_2$SO$_4$. The organic layer was evaporated to yield the 1.27 g (69%) Pt(II) μ-dichloro-bridged dimer as a yellow powder.

The Pt(II) μ-dichloro-bridged dimer (1.25 g, 1.62 mmol) and Et$_2$S (5.0 mL, 46 mmol) in dry chloroform was stirred at 50° C. for 12 hours. The reaction mixture was cooled down and evaporated to yield an oily yellow residue. The yellow residue was chromatographed on silica gel with dichloromethane to yield 0.56 g (72%) of PtCl(phpy)(Et$_2$S) as a yellow powder.

A solution of lithiated 1a [from 2-thienylpyridine (0.084 g, 0.526 mmol) and 1.6 M t-Buli (0.65 mL, 1.1 mmol) in ether at −78° C.] in ether at −78° C. was added dropwise to a stirred solution of PtCl (phpy)(Et$_2$S) (0.250 g, 0.526 mmol) in diethylether and THF at −78° C. After the solution was stirred for 30 min at −78° C., the temperature was allowed to rise slowly to 0° C. The reaction mixture was hydrolyzed (H$_2$O) at 0° C. The organic phase was washed with NaCl solution and the aqueous phase extracted with dichloromethane. The combined extracts were dried (MgSO$_4$) and evaporated to yield a red oily residue. The residue was chromatographed on silica gel using dichloromethane/hexane (3:2) as the eluant to give 0.125 g (47%) of 5 as a red powder. $^1$H NMR (500 MHz, CDCl$^3$): δ 8.76 (d, 1H), 8.61 (d, 1H), 8.26 (td, 1H), 7.86 (m, 2H), 7.20 (m, 2H), 7.62 (d, 1H), 7.50 (m, 2H), 7.27 (m, 2H), 7.13 (m, 2H). HRMS calc. for C$_{20}$H$_{14}$N$_2$PtS (M)$^+$, 509.0516; found, 509.0503.

Example 17

Figure 5:
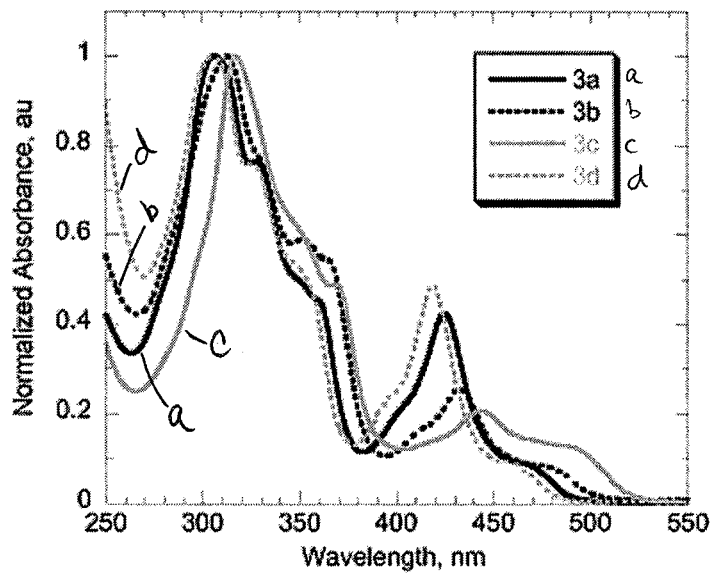
FIG. 5 shows the normalized UV/vis spectra of (a) complex 3a, (b) complex 3b, (c) complex 3c, and (d) complex 3d, in THF.
Figure 6:
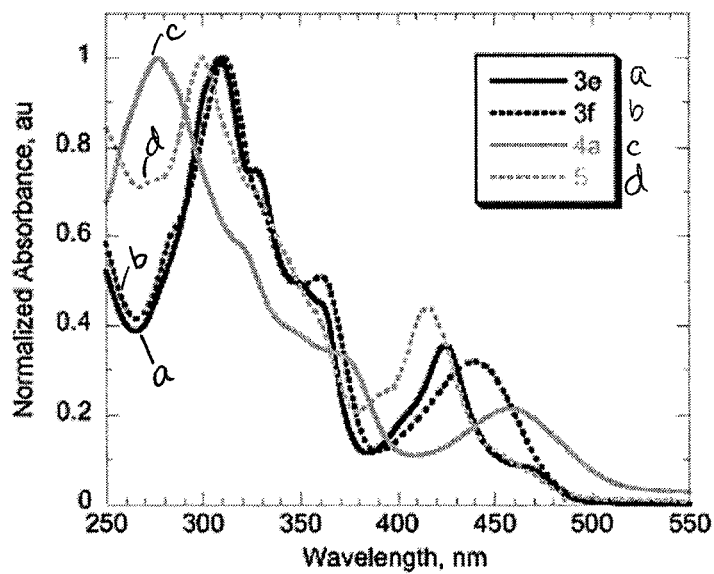
FIG. 6 shows the normalized UV/vis spectra of (a) complex 3e, (b) complex 3f, (c) complex 4a, and (d) complex 5, in THF.

The photophysical properties of the platinum (II) complexes were investigated in deoxygenated, room-temperature fluid solution and in 77K 2-methyltetrahydrofuran glasses. Table 1 summarizes the photophysical properties of the platinum (II) complexes. FIG. 5 shows the normalized UV/vis spectra of (a) complex 3a, (b) complex 3b, (c) complex 3c, and (d) complex 3d, in THF, and FIG. 6 shows the normalized UV/vis spectra of (a) complex 3e, (b) complex 3f, (c) complex 4a, and (d) complex 5, in THF. Several of the complexes investigated showed sharp and distinct MLCT transitions with extinction coefficients of approximately 10$^4$, as is characteristic for the parent Pt(thpy)$_2$ complex (3a). These bands also showed moderate negative solvatochromism, in that more polar solvents gave blue-shifted MLCT bands. For example, complex 3a exhibited an MLCT maximum at 419 nm in acetone, but, in toluene, was red-shifted to 430 nm. Also, increasing the electron density (3b, 3c) or the conjugation lengths (4a) of the ligands tended to cause a red shift in the absorbance bands.

Figure 7:
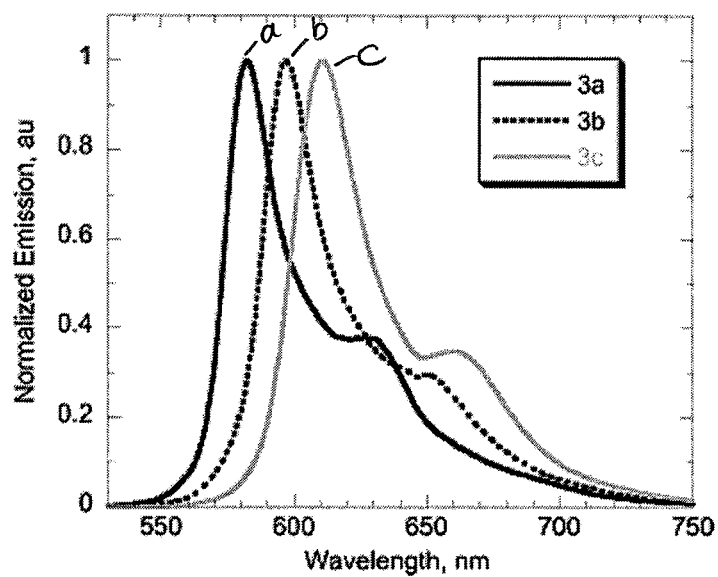
FIG. 7 shows the emission spectra of (a) complex 3a, (b) complex 3b, (c) complex 3c, at room temperature in THF.
Figure 8:
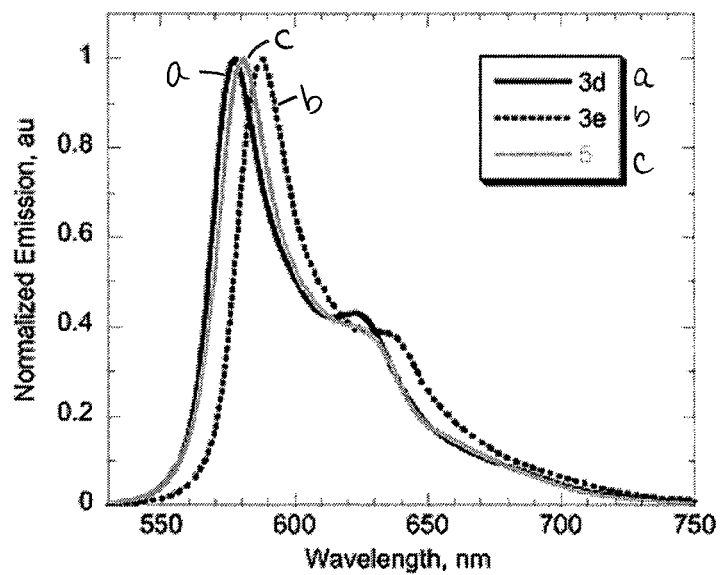
FIG. 8 shows the emission spectra of (a) complex 3a, (b) complex 3b, (c) complex 3c, at room temperature in THF.

FIG. 7 shows the emission spectra of (a) complex 3a, (b) complex 3b, (c) complex 3c, at room temperature in THF, and FIG. 8 shows the emission spectra of (a) complex 3a, (b) complex 3b, (c) complex 3c, at room temperature in THF. Most of the Pt(II) complexes displayed moderate to strong phosphorescence intensity (with quantum yields of emission between 0.05 and 0.30) in room temperature, deoxygenated fluid solution. The emissive complexes were observed to phosphoresce in the orange or red region of the visible spectrum with lifetimes on the timescale of 5-15 microseconds at ambient temperature. The lower quantum yield and biexponential character of complex 5 may be due to the presence of a competing, non-emissive state involving the phenylpyridine ligand The Pt(II) complexes showed only weak solvatochromism in their phosphorescence energy. The rigidochromic effect on the emission of these complexes is a small value of 9±3 nm upon freezing the sample in a 2-methyltetrahydrofuran glass. The rigid glass did not allow reorganization of solvent dipoles upon generation of an excited state, and gave a strongly blue-shifted spectrum of complexes that emit from a charge-transfer state. Without wishing to be bound by theory, such trends, coupled with the vibronic structure observed in the room temperature phosphorescence spectra, suggest that the emissive state of the complexes may be an admixture of an MLCT state and an intraligand pi-pi* state. This behavior was similar to other Pt(II) cyclometalated complexes.

Not all of the complexes, however, exhibited strong emission at room temperature. Complexes 3f and 4a exhibited phosphorescence quantum yields of less than 1 percent. As demonstrated with complex 3f, the addition of a methyl group on the pyridine ring almost completely eliminated phosphorescence. The relatively small effect of including a more powerful donor (e.g., methoxy group) in complex 3c suggested that phosphorescence attenuation may be due to steric congestion of the square plane around the metal center. The strong room temperature emission of complexes 3d and 3e also support the hypothesis that steric congestion may be the reason for the very weak emission of complexes 3f and 4a. Complex 3f displayed similar behavior to complexes 3d and 3e, the only difference being that the methyl groups meta or para to the pyridine nitrogen were not expected to have repulsive interactions in the square plane. Complexes 3f and 4a also gave broadened MLCT absorbance bands, suggesting that there may be more conformational variation in these non-emissive complexes.

Example 18

Figure 9A:
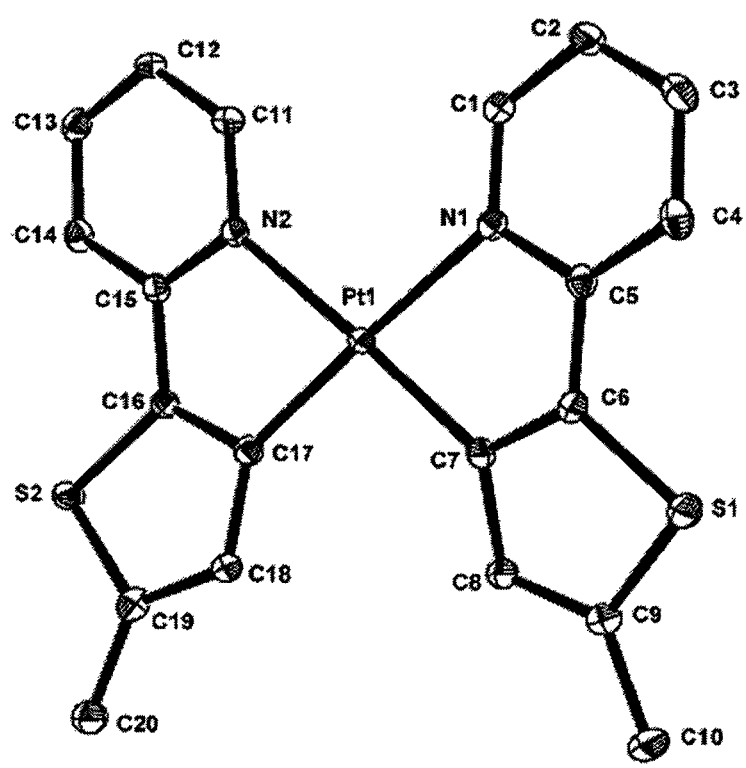
FIG. 9A shows the X-ray crystal determination for complex 3b.
Figure 9B:
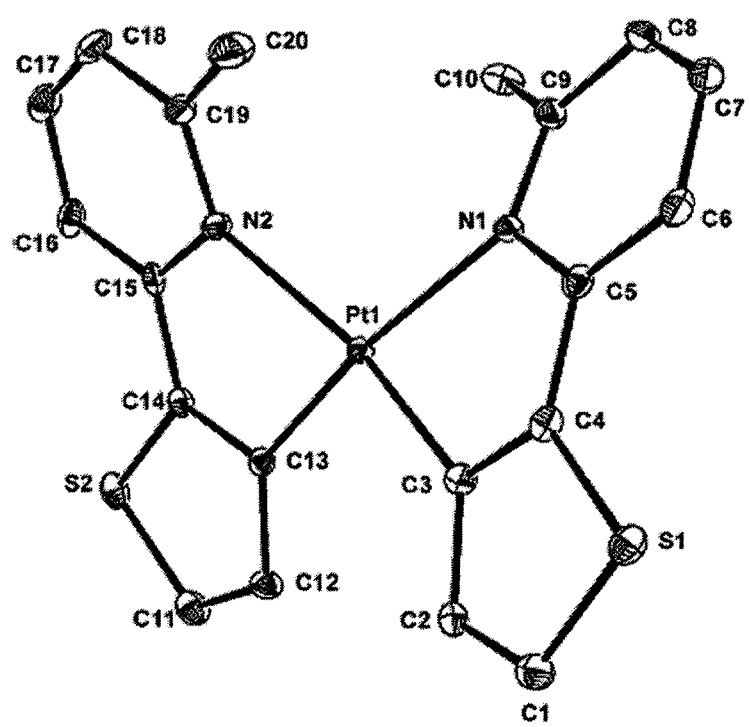
FIG. 9B shows the X-ray crystal determination for complex 3f.

In order to directly observe the effects of interligand steric congestion around the platinum metal center, single crystal x-ray structures were obtained for complexes 3b, 3f, and 5, with the crystallographic parameters shown in Table 2. FIG. 9A shows the ORTEP diagram of the crystal structures of complex 3b, and FIG. 9B shows the ORTEP diagram of the crystal structures of complex 3f. Thermal ellipsoids are at 50% probability, and hydrogen atoms were omitted for clarity. As shown in FIG. 9A, complex 3b is only slightly distorted out of a square planar geometry, while 3f, on the other hand, is severely distorted away from ideal square plane geometry because of the steric repulsion between the methyl groups ortho to the nitrogen on the pyridine ring (FIG. 9B).

While suitable crystals from the benzthiophene-substituted complexes were unable to be grown, simple molecular mechanics modeling indicated that the aryl hydrogen atoms in the 4-position of the thianapthene ring system in complex 4a were predicted to have similar steric interactions in a square planar geometry, forcing the complex into a highly distorted conformation. Certain quinoline-substituted bis-cyclometalated heavy metal group 10 $d^8$ complexes have been shown to have a severely twisted geometry for similar reasons. Such intramolecular repulsions may lead to enhanced non-radiative relaxation of the excited state through additional twisting and vibration.

TABLE 2

Crystallography Parameters.

|  | 3b | 3f | 5 |
|---|---|---|---|
| Empirical formula | $C_{20}H_{16}N_2PtS_2$ | $C_{20}H_{16}N_2PtS_2$ | $C_{20}H_{14}N_2PtS$ |
| Color | Orange | Orange | Red |
| Mr | 543.56 | 543.56 | 509.48 |
| Crystal size | 0.02 × 0.05 × 0.02 | 0.20 × 0.20 × 0.10 | 0.10 × 0.05 × 0.04 |
| T(K) | 100 (2) | 100 (2) | 100 (2) |
| λ(MoKα) | 0.71073 | 0.71073 | 0.71073 |
| Crystal | Triclinic | Monoclinic | Triclinic |
| Space group | P-1 | P2(1) | P-1 |
| a [Å] | 6.9633 (12) | 16.0087 (10) | 9.8404 (8) |
| b [Å] | 10.9345 (18) | 9.0397 (5) | 18.3388 (18) |
| c [Å] | 11.3463 (19) | 24.8119 (15) | 18.4798 (17) |
| α (°) | 99.492 (3) | 90 | 74.296 (3) |
| β (°) | 96.613 (3) | 104.853 (2) | 80.151 (3) |
| γ (°) | 90.630 (3) | 90 | 86.066 (3) |

TABLE 1

Photophysical parameters of Pt(II) complexes 3-5, where (a) the first maximum is ligand-centered absorption and the second maximum is MLCT, (b) photophysical parameters were not determined due to weak signal, and (c) multi-exponential decay occurred.

| | Room Temperature Solution (THF) | | | | 77 K Glass (2-MeTHF) | |
|---|---|---|---|---|---|---|
| Complex | $\lambda_{max}$ (UV/vis)[a] | $\lambda_{max}$ (Phos) | $\xi_p$ | $\Phi_p$ | $\lambda_{max}$ (Phos) | $\xi_p$ |
| 3a | 306, 425 nm | 582 nm | 5.5 μs | 0.24 | 575 nm | 10.3 μs |
| 3b | 312, 433 nm | 599 nm | 13.2 μs | 0.29 | 590 nm | 13.0 μs |
| 3c | 317, 443 nm | 613 nm | 13.6 μs | 0.30 | 605 nm | 14.2 μs |
| 3d | 306, 419 nm | 578 nm | 6.0 μs | 0.24 | 569 nm | 10.9 μs |
| 3e | 309, 425 nm | 588 nm | 6.4 μs | 0.22 | 578 nm | 9.7 μs |
| 3f | 311, 438 nm | 582 nm | b | <0.01 | 572 nm | 15.2 μs |
| 4a | 277, 458 nm | 630 nm | b | <0.01 | 626 nm | 8.7 μs |
| 5 | 300, 415 nm | 581 nm | c | 0.05 | 567 nm | 13.2 μs |

TABLE 2-continued

Crystallography Parameters.

| | 3b | 3f | 5 |
|---|---|---|---|
| V [Å$^3$] | 846.0 (2) | 3470.7 (4) | 3162.2 (5) |
| Z | 2 | 8 | 8 |
| ρ calcd | 2.134 | 2.081 | 2.140 |
| μ [mm$^{-1}$] | 8.544 | 8.331 | 9.009 |
| F (000) | 520 | 2080 | 1936 |
| Transmission range | 0.6746-0.8477 | 0.2866-0.4896 | 0.4661-0.7145 |
| 2θ range | 3.66° < 2θ < 58.26° | 1.7° < 2θ < 59.14° | 2.32° < 2θ < 56.56° |
| Measured reflections | 18469 | 67464 | 18990 |
| Unique reflections | 4549 | 19402 | 18990 |
| Parameters | 228 | 910 | 1584 |
| Gof (for F$^2$) | 1.052 | 1.024 | 1.160 |
| R$_1$[I > 2σ(I)], R1 all | 0.0165, 0.0181 | 0.0198, 0.0208 | 0.0500, 0.0704 |
| wR$_2$[I > 2σ(I)], wR$_2$ | 0.0389, 0.0398 | 0.0464, 0.0468 | 0.0886, 0.0924 |
| Δρ$_{max/min}$ | 1.267, -0.502 | 1.833, -1.140 | 2.708, -1.887 |

$^a$ R1 = Σ(F$_o$ − F$_c$)/ΣF$_o$; I > 2σ(I); wR2 = {Σw(F$_o^2$ − F$_c^2$)$^2$/Σw(F$_o^2$)$^2$}$^{1/2}$

Example 19

Figure 10:
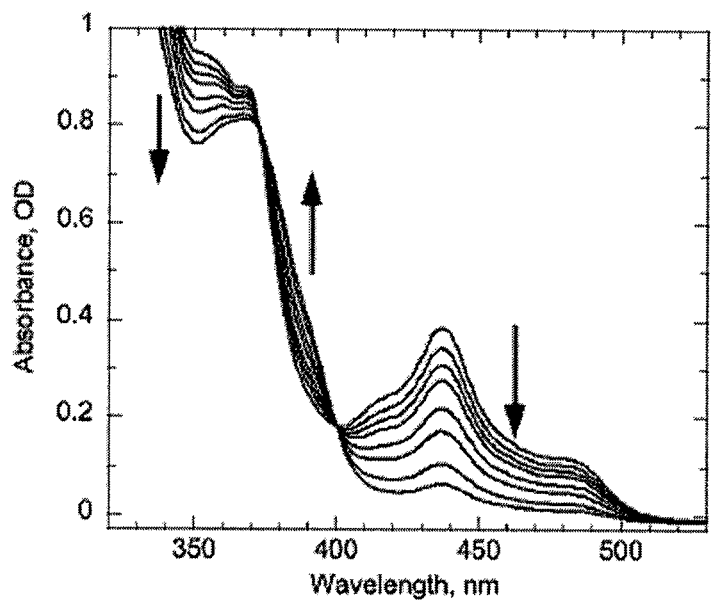
FIG. 10 shows the UV/vis spectra of complex 3b during its reaction with 1.0 M MeI in benzene.
Figure 11:
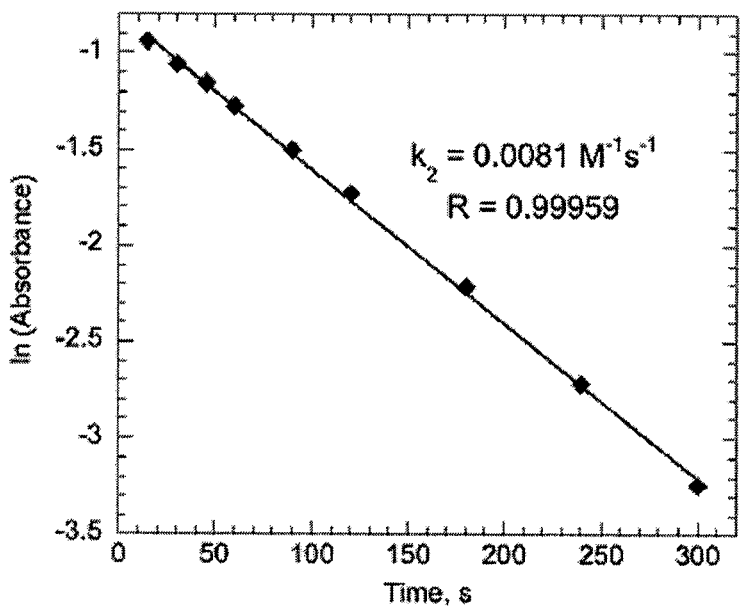
FIG. 11 shows a pseudo-first order rate plot for complex 3b in 1.0 MeI/benzene.

The metal complexes were evaluated for their ability to undergo oxidative addition with an electrophile in solution. All of the synthesized complexes were observed to participate in oxidative addition reactions under ambient conditions. FIG. 10 shows the shows the progress of a reaction with 3b with 1.0 M methyl iodide under pseudo-first order conditions in benzene as followed by absorbance spectroscopy. Times elapsed, in seconds, are 15, 30, 45, 60, 90, 120, 180, 240, and 300. FIG. 11 shows a pseudo-first order rate plot for 3b in 1.0 MeI/benzene, wherein the calculated bimolecular rate constant was 0.0081 M$^{-1}$s$^{-1}$. The isosbestic points shown in FIG. 10 and the pseudo-first order kinetics shown in FIG. 11 illustrate the clean oxidative addition of complex 3b to methyl iodide. The reaction rate displays strong solvent dependence, which may be indicative of a highly polar transition state and an S$_N$2-type mechanism.

Figure 12:
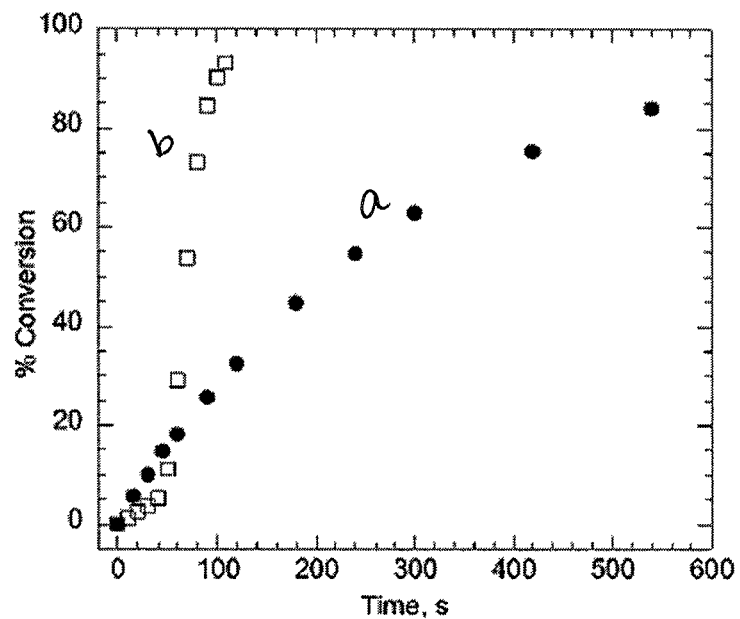
FIG. 12 shows the plot of conversion versus time as determined by UV/vis, for the reaction between complex 3a and (a) MeI or (b) BrCN, in benzene.
Figure 13:
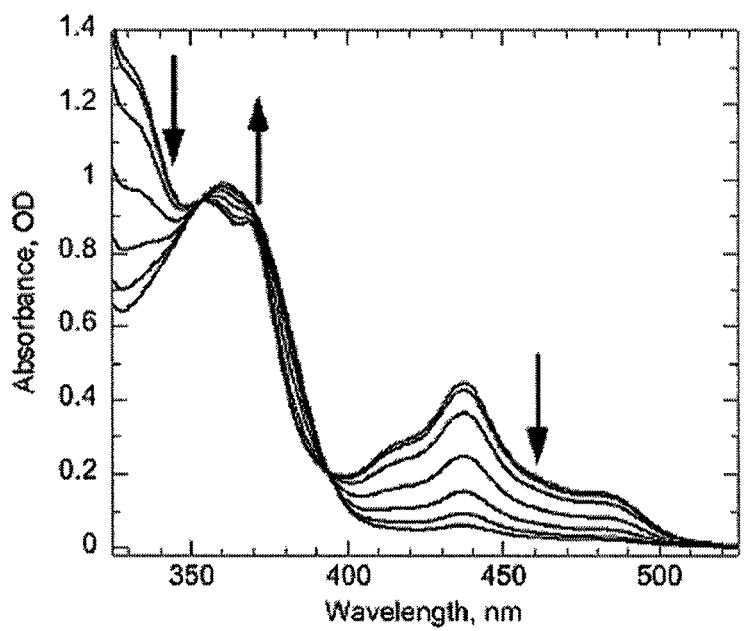
FIG. 13 shows the UV/vis spectra of complex 3b during its reaction with 0.00013 M BrCN in benzene.
Figure 14:
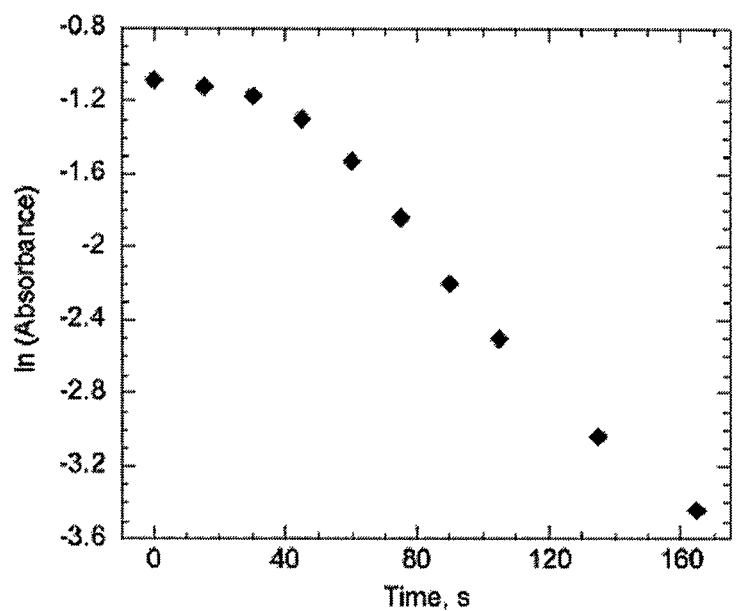
FIG. 14 shows the first-order kinetic plot for the reaction of complex 3b with BrCN (2.4E-4 M) in benzene.

Upon adding cyanogen bromide to these complexes under similar conditions, several important differences were apparent. First, the reaction with cyanogen bromide was observed to proceed much faster than that with methyl iodide. FIG. 12 shows percent conversion as a function of reaction time for (a) methyl iodide (1.0 M) and (b) cyanogen bromide (0.00013 M) with complex 3a. FIG. 13 shows the UV/vis spectra of 3b during the reaction with 0.00013 M BrCN in benzene, where the times elapsed are in 20 second intervals. The cyanogen bromide reaction proceeded to completion much faster than the reaction with MeI, even though the relative concentration of BrCN was almost 10$^4$ times smaller. The non-polar solvent benzene was used to more effectively mimic a solid-state environment, which would be used for sensing purposes, than a more polar solvent. The UV/vis profiles of these reactions also showed clean (e.g., "well-behaved") isosbestic points, disappearance of the Pt(II) MLCT band, and growth of an absorbance at approximately 350 nm, characteristic of bis-cyclometalated Pt(IV) complexes. Second, in addition to a much faster reaction rate in solution, the kinetic profiles of these reactions with CNBr were not seen to follow a simple kinetic model. FIG. 14 shows the pseudo-first order rate plot for the reaction of complex 3b with 0.00024 M CNBr in benzene. The reaction was observed to accelerate very quickly following an initial induction period, indicating that a different mechanism may be taking place, rather than the S$_N$2 type invoked for the oxidative addition with methyl iodide. A third difference observed between the reactions with CNBr and MeI was the lack of strong solvent polarity dependence on rate of reaction of the Pt(II) complexes and CNBr. Upon switching from toluene to acetone, the initial reaction rate only increased by approximately 50%.

Figure 15:
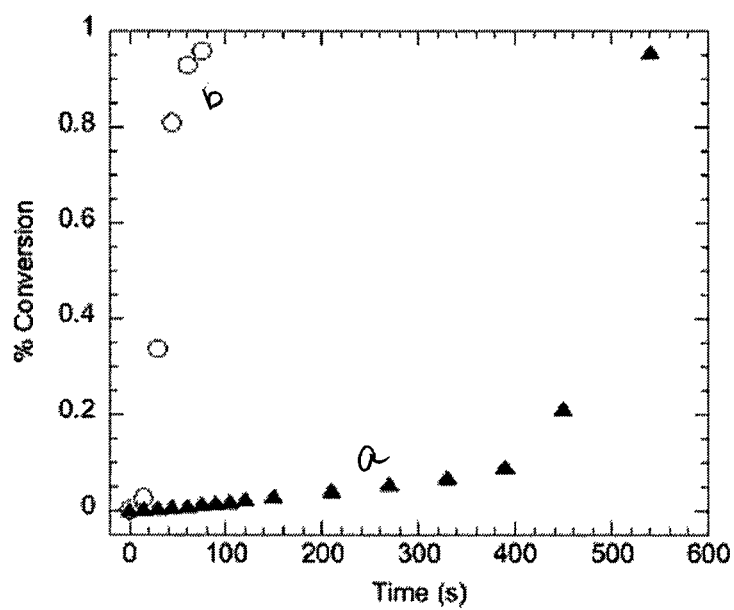
FIG. 15 shows the percentage conversion of complex 3a in (a) toluene or (b) benzene, in the presence of 0.00024 M BrCN.

Without wishing to be bound by theory, the key differences in the CNBr reactions may be indicative of a radical, potentially chain, mechanism operating in this reaction. This may be further supported by the observation that the reaction proceeds to completion much faster in benzene than in toluene, as shown by the percentage conversion of complex 3a in (a) toluene or (b) benzene, in the presence of 0.00024 M BrCN. (FIG. 15) This suggests that an intermediate, radicals may abstract a benzylic hydrogen atoms from toluene, thereby inhibiting the reaction.

To ensure that oxidative addition, and not complex decomposition, was occurring, the reaction between complex 3a and BrCN was performed on a preparative (~30 mg) scale. Upon mixing the two in THF, a colorless product immediately precipitated. The major product (of 2 by TLC) was isolated by filtration and washing with dichloromethane. Mass analysis of the isolated product showed the desired molecular ion for Pt(thpy)$_2$(Br)(CN) with the expected fragmentation pattern. NMR analysis was unable to be performed due to limited solubility of the complex. No free ligand was observed upon addition of BrCN. Although the product was not emissive in room temperature fluid solution, it was strongly emissive at 77K with photophysical parameters consistent with a bis-cyclometalated Pt(IV) complex. This included a highly structured emission spectrum with a maximum in the green region of the visible spectrum and an excited state lifetime of about 400 microseconds.

Example 21

Figure 16:
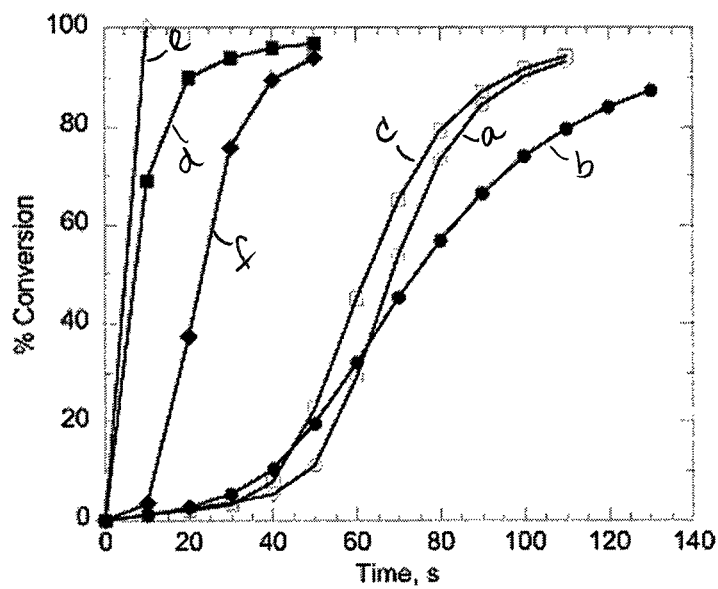
FIG. 16 shows the conversion percentages of (a) complex 3a, (b) complex 3b, (c) complex 3e, (d) complex 3f, (e) complex 4a, and (f) complex 5, as a function of time in 0.00013 M BrCN/benzene.

Structure-reactivity trends between different Pt(II) complexes and BrCN were analyzed. The trends were found to yield similar results to the study of photophysical properties. The most reactive complexes were those that incorporated interligand steric congestion into the square plane of the complex (e.g., complexes 3f, 4a) even at stoichiometric concentrations of BrCN. FIG. 16 shows the conversion percentages of (a) complex 3a, (b) complex 3b, (c) complex 3e, (d) complex 3f, (e) complex 4a, and (f) complex 5, as a function of time in 0.00013 M BrCN/benzene. The increase in the energy of the sterically crowded complexes was shown to decrease the activation barrier for oxidative addition, increasing the rate at which these heavily distorted complexes are converted to octahedral products. The fact that the least emissive Pt(II) complexes are the most reactive towards oxidative addition with BrCN may be advantageous for "turn-on" phosphorescence-based sensing schemes, since excessive phosphorescence from the starting "off" state may increase the background signal on top of which the measurement must be made. Interestingly, the heteroleptic complex 5 also proceeds to completion faster than the parent homoleptic complex 3a.

In contrast to the structure-reactivity trend with BrCN, the more sterically hindered complexes (e.g., complexes 3f, 4a) exhibited bimolecular rate constants with methyl iodide (in benzene) that were approximately 4-10 times smaller than the unstrained systems (Table 3). This was likely not due to an electronic effect because complexes 3d and 3e, which have methyl groups in different positions on the pyridine ring, did not show behavior similar to that of 3f. Rather, the smaller bimolecular rate constants suggested that the transition state for $S_N2$ type oxidative addition to these complexes exacerbated the preexisting steric congestion, possibly by forcing the complex into a square-pyramidal geometry, whereas the transition state for the reaction with BrCN relieved the unfavorable interactions. This difference may be particularly useful for sensing, as it could impart additional selectivity for cyanogen halides over interferents that react by the $S_N2$-type mechanism.

TABLE 3

Bimolecular rate constants of platinum complexes with MeI in benzene.

| Complex | $k_2$ (M$^{-1}$s$^{-1}$) |
| --- | --- |
| 11a | $3.4 \times 10^{-3}$ |
| 11b | $8.1 \times 10^{-3}$ |
| 11c | $4.8 \times 10^{-3}$ |
| 11d | $8.8 \times 10^{-3}$ |
| 11e | $5.1 \times 10^{-3}$ |
| 11f | $0.82 \times 10^{-3}$ |
| 12a | $0.93 \times 10^{-3}$ |
| 13 | $5.8 \times 10^{-3}$ |

Example 21

Films of the metal complexes were then made and their photophysical properties were investigated. The platinum complexes were doped into a polymer matrix in order to create a substance with desirable material properties that could be readily cast into films. Each film was prepared by spin-casting a dichloromethane solution containing a mixture of poly(methyl methacrylate) (PMMA) and the desired Pt(II) complex (10% w/w relative to PMMA). Transparent, glassy, highly phosphorescent thin films were obtained, many of which were highly emissive even under ambient conditions. The glassy PMMA excluded enough oxygen to allow radiative decay of the triplet excited states to be kinetically competitive with oxygen-induced quenching.

Figure 17:
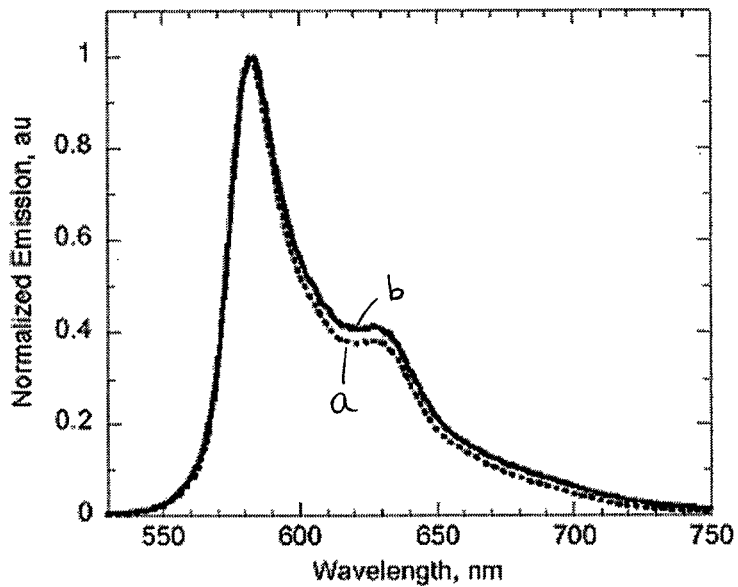
FIG. 17 shows the normalized emission spectra of complex 3a in (a) degassed THF solution and (b) doped into PMMA films (10% w/w).

FIG. 17 shows the normalized emission spectra of complex 3a in (a) degassed THF solution and (b) doped into PMMA films (10% w/w). As illustrated in FIG. 17, the films exhibited emission spectra having similar shapes to the emission spectra of the complexes obtained in solution. This indicates that, at 10% loading, the amount of intermolecular communication between the metal complexes was negligible. In addition, complexes 3f and 4a, which were not emissive in room temperature solution but were emissive at 77 K, showed phosphorescence spectra in the PMMA films that were in the same spectral region as the emission spectra of the complexes at 77K in solution. This may be attributed to the rigid PMMA matrix, which may inhibit intramolecular conformational changes that lead to non-radiative deactivation of the excited states of these strained molecules.

Example 22

Figure 18:
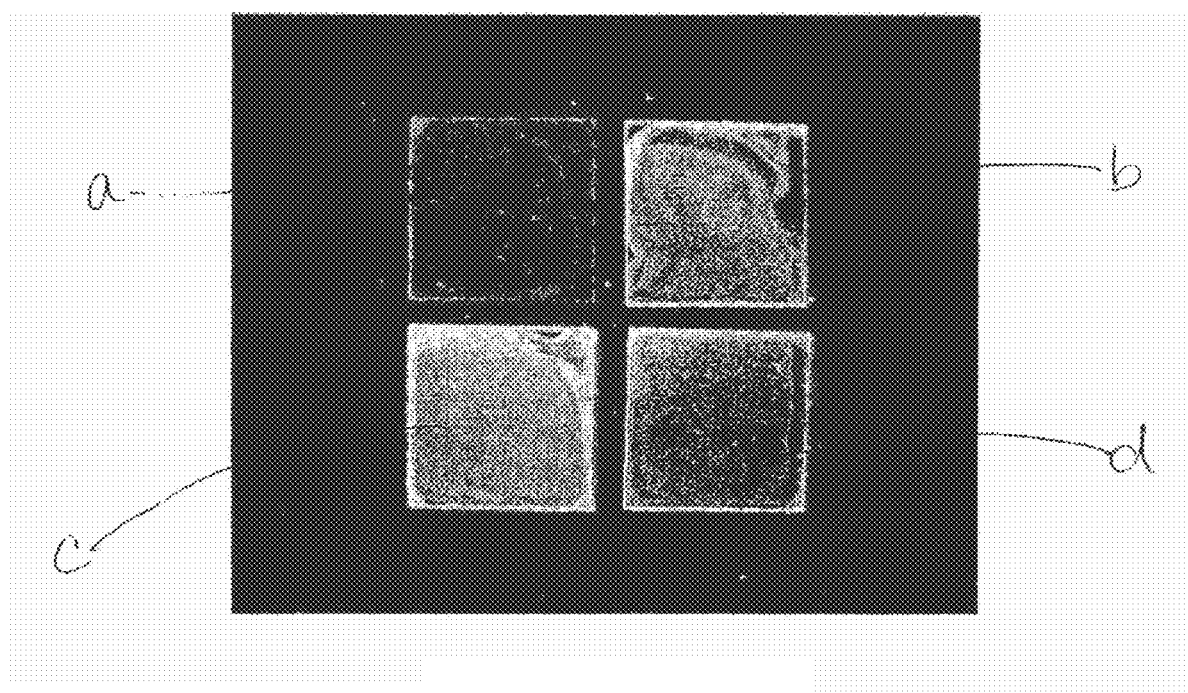
Figure 19:
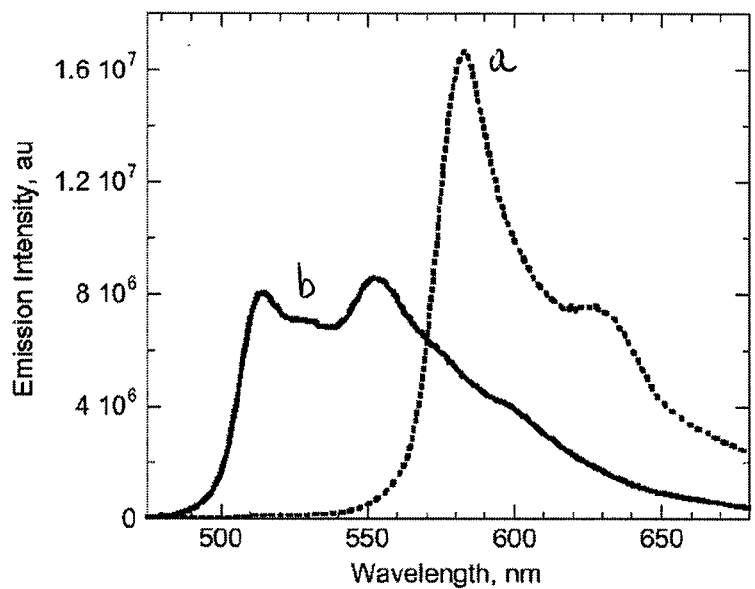
FIG. 19 shows the PMMA film emission spectra of complex 3a (a) before and (b) after exposure to BrCN vapor for 15 seconds.
Figure 20:
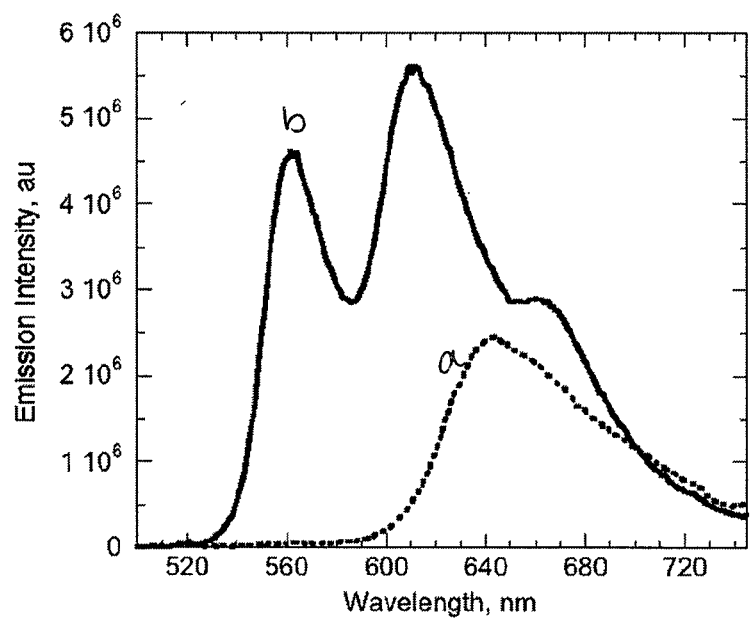
FIG. 20 shows the PMMA film emission spectra of complex 4a (a) before and (b) after exposure to BrCN vapor for 15 seconds.

The solid-state phosphorescence sensing ability of the metal complexes was investigated. Upon exposing the doped PMMA films (described in Example 21) to saturated BrCN vapor, complete conversion to the corresponding platinum (IV) complexes occurred within seconds. The blue-shifted emission of the product was apparent, both spectroscopically and visually. The spectral features of the products in the solid state were consistent with the characteristic ligand-centered platinum (IV) emission, both in spectral position and the relative intensities of the vibronic bands. FIG. 18A shows a picture of a PMMA film containing 3a and FIG. 18B shows a picture of a PMMA film containing 3a that has been exposed to saturated BrCN vapor for 15 seconds. FIG. 18C shows a picture of a PMMA film containing 4a and FIG. 18D shows a picture of a PMMA film containing 4a that has been exposed to saturated BrCN vapor for 15 seconds. FIG. 19 shows the PMMA film emission spectra of 3a (a) before and (b) after exposure to BrCN vapor for 15 seconds. FIG. 20 shows the PMMA film emission spectra of 4a (a) before and (b) after exposure to BrCN vapor for 15 seconds. The spectra in FIG. 19-20 illustrate how using a strong spectral blue-shift as the sensing signal gives a turn-on signal with virtually no background ("dark-field").

This feature may be desirable in any sensing system for maximum sensitivity to trace quantities of analyte. Preliminary experiments demonstrating trace (part-per-million) sensitivity to the cyanogen halides have shown modest sensitivity to 10 ppm BrCN vapor.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method for determination of an analyte, comprising:
exposing a metal complex having a luminescence emission to a sample suspected of containing an analyte, wherein the analyte, if present, interacts with the metal complex via an oxidative addition reaction to produce a change in the luminescence emission of the metal complex;
determining the change in luminescence emission of the metal complex, wherein the change in luminescence emission comprises a blue-shifted change in the wavelength of the luminescence emission; and
determining the presence or absence of the analyte based on the change in luminescence emission of the metal complex.

2. A method as in claim 1, wherein, in the absence of analyte, the metal complex has a substantially square planar geometry, and wherein the analyte, if present, interacts with the metal complex to produce a change in the substantially square planar geometry of the metal complex.

3. A method as in claim 2, wherein the change in the substantially square planar geometry of the metal complex comprises formation of a substantially octahedral geometry of the metal complex.

4. A method as in claim 1, wherein the metal complex has the structure,

wherein M is a metal, and $L^1$ and $L^2$ can be the same or different and, when bound to the metal, $L^1$ and $L^2$ are bidentate cyclometallated ligands.

5. A method as in claim 4, wherein M is platinum, iridium, or palladium.

6. A method as in claim 4, wherein M is platinum.

7. A method as in claim 4, wherein at least one bidentate cyclometallated ligand has the structure,

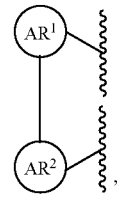

wherein $Ar^1$ and $Ar^2$ can be the same or different and are aryl or heteroaryl, optionally substituted, or $Ar^1$ and $Ar^2$ together form a fused polycyclic aromatic group, optionally substituted.

8. A method as in claim 4, wherein $L^1$ and $L^2$ can be the same or different and are phenylthiophene, thienylpyridine, thianapthylpyridine, or substituted derivatives thereof.

9. A method as in claim 1, wherein the luminescence emission is phosphorescence emission.

10. A method as in claim 1, wherein the analyte is an electrophilic species.

11. A method as in claim 1, wherein the analyte is an alkyl halide or cyanogen halide.

12. A method as in claim 1, wherein the analyte is cyanogen bromide, cyanogen chloride, benzyl bromide, ethyl bromide, methyl iodide, chloroform, or dichloromethane.

13. A method as in claim 1, wherein, in the absence of analyte, the metal complex has a first emission, and wherein the analyte, if present, interacts with the metal complex to produce a second emission such that the wavelength of the first emission is separated from the wavelength of the second emission by at least 30 nm.

14. A method as in claim 13, wherein the wavelength of the first emission is separated from the wavelength of the second emission by at least 50 nm.

15. A method as in claim 13, wherein the wavelength of the first emission is separated from the wavelength of the second emission by at least 100 nm.

16. A method as in claim 13, wherein the wavelength of the first emission is separated from the wavelength of the second emission by at least 150 nm.

17. A method for determination of an analyte, comprising:
exposing a metal complex having a luminescence emission to a sample suspected of containing an analyte, wherein the analyte, if present, interacts with the metal complex to produce a change in the luminescence emission of the metal complex,
wherein the metal complex has the structure,

wherein M is a metal, and $L^1$ and $L^2$ can be the same or different and, when bound to the metal, $L^1$ and $L^2$ are bidentate cyclometallated ligands;

determining the change in luminescence emission of the complex, wherein the change comprises a blue-shifted change in the wavelength of the luminescence emission; and determining the presence or absence of the analyte based on the change in luminescence emission of the complex.

18. A method as in claim 17, wherein, in the absence of analyte, the metal complex has a substantially square planar geometry, and wherein the analyte, if present, interacts with the metal complex to produce a change in the substantially square planar geometry of the metal complex.

19. A method as in claim 18, wherein the change in the substantially square planar geometry of the metal complex comprises formation of a substantially octahedral geometry of the metal complex.

20. A method as in claim 17, wherein M is platinum, iridium, or palladium.

21. A method as in claim 17, wherein M is platinum.

22. A method as in claim 17, wherein at least one bidentate cyclometallated ligand has the structure,

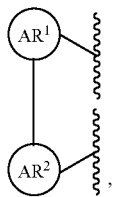

wherein $Ar^1$ and $Ar^2$ can be the same or different and are aryl or heteroaryl, optionally substituted, or $Ar^1$ and $Ar^2$ together form a fused polycyclic aromatic group, optionally substituted.

23. A method as in claim 17, wherein $L^1$ and $L^2$ can be the same or different and are phenylthiophene, thienylpyridine, thianapthylpyridine, or substituted derivatives thereof.

24. A method as in claim 17, wherein the luminescence emission is phosphorescence emission.

25. A method as in claim 17, wherein the analyte is an electrophilic species.

26. A method as in claim 17, wherein the analyte is an alkyl halide or cyanogen halide.

27. A method as in claim 17, wherein the analyte is cyanogen bromide, cyanogen chloride, benzyl bromide, ethyl bromide, methyl iodide, chloroform, or dichloromethane.

28. A method as in claim 17, wherein, in the absence of analyte, the metal complex has a first emission, and wherein the analyte, if present, interacts with the metal complex to produce a second emission such that the wavelength of the first emission is separated from the wavelength of the second emission by at least 30 nm.

29. A method as in claim 28, wherein the wavelength of the first emission is separated from the wavelength of the second emission by at least 50 nm.

30. A method as in claim 28, wherein the wavelength of the first emission is separated from the wavelength of the second emission by at least 100 nm.

31. A method as in claim 28, wherein the wavelength of the first emission is separated from the wavelength of the second emission by at least 150 nm.

* * * * *